(12) United States Patent
Butson et al.

(10) Patent No.: US 8,812,126 B2
(45) Date of Patent: *Aug. 19, 2014

(54) SYSTEM AND METHOD TO DEFINE TARGET VOLUME FOR STIMULATION OF THE SPINAL CORD AND PERIPHERAL NERVES

(71) Applicant: The Cleveland Clinic Foundation, Cleveland, OH (US)

(72) Inventors: Christopher R. Butson, Wauwatosa, WI (US); Cameron C. McIntyre, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 28 days.

This patent is subject to a terminal disclaimer.

(21) Appl. No.: 13/765,306

(22) Filed: Feb. 12, 2013

(65) Prior Publication Data

US 2013/0150922 A1 Jun. 13, 2013

Related U.S. Application Data

(60) Continuation of application No. 12/881,903, filed on Sep. 14, 2010, now Pat. No. 8,594,800, which is a continuation-in-part of application No. PCT/US2009/066821, filed on Dec. 4, 2009, application No. 13/765,306, which is a continuation-in-part of application No. 13/480,858, filed on May 25, 2012, now Pat. No. 8,538,543, which is a division of application No. 11/606,260, filed on Nov. 28, 2006, now Pat. No. 8,209,027.

(60) Provisional application No. 61/120,006, filed on Dec. 4, 2008, provisional application No. 60/740,031, filed on Nov. 28, 2005.

(51) Int. Cl.
*A61N 1/08* (2006.01)
*A61B 5/05* (2006.01)
*A61N 1/05* (2006.01)

(52) U.S. Cl.
CPC ............ *A61N 1/0534* (2013.01); *A61N 1/08* (2013.01)
USPC .......................................... 607/59; 600/407

(58) Field of Classification Search
USPC .......................................... 607/59; 600/407
See application file for complete search history.

(56) References Cited

U.S. PATENT DOCUMENTS

| 4,341,221 A | 7/1982 | Testerman |
| 5,099,846 A | 3/1992 | Hardy |

(Continued)

FOREIGN PATENT DOCUMENTS

| EP | 1372780 A2 | 1/2004 |
| WO | 02065896 A2 | 8/2002 |
| WO | 03086185 A1 | 10/2003 |

OTHER PUBLICATIONS

Butson, C. R., et al., "StimExplorer: Deep brain stimulation parameter selection software system," In: Neuromodulation, De Sakas, B Simpson and E Krames (eds), Springer-Verlag., (2006), pp. 569-574.

(Continued)

*Primary Examiner* — Carl H Layno
*Assistant Examiner* — Jon Eric C Morales
(74) *Attorney, Agent, or Firm* — Kenyon & Kenyon LLP

(57) ABSTRACT

One embodiment provides a computer-implemented method that includes storing a volume of tissue activation (VTA) data structure that is derived from analysis of a plurality of patients. Patient data is received for a given patient, the patient data representing an assessment of a patient condition. The VTA data structure is evaluated relative to the patient data to determine a target VTA for achieving a desired therapeutic effect for the given patient.

29 Claims, 17 Drawing Sheets

(56) References Cited

U.S. PATENT DOCUMENTS

| | | |
|---|---|---|
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,782,762 A | 7/1998 | Vining |
| 5,938,688 A | 8/1999 | Schiff |
| 6,066,163 A | 5/2000 | John |
| 6,083,162 A | 7/2000 | Vining |
| 6,106,460 A | 8/2000 | Panescu et al. |
| 6,146,390 A | 11/2000 | Heilbrun et al. |
| 6,240,308 B1 | 5/2001 | Hardy et al. |
| 6,289,239 B1 | 9/2001 | Panescu et al. |
| 6,301,492 B1 | 10/2001 | Zonenshayn |
| 6,310,619 B1 | 10/2001 | Rice |
| 6,343,226 B1 | 1/2002 | Sunde et al. |
| 6,351,675 B1 | 2/2002 | Tholen et al. |
| 6,389,311 B1 | 5/2002 | Whayne et al. |
| 6,421,566 B1 | 7/2002 | Holsheimer |
| 6,463,328 B1 | 10/2002 | John |
| 6,491,699 B1 | 12/2002 | Henderson et al. |
| 6,539,263 B1 | 3/2003 | Schiff et al. |
| 6,560,490 B2 | 5/2003 | Grill et al. |
| 6,622,048 B1 | 9/2003 | Mann et al. |
| 6,675,046 B2 | 1/2004 | Holsheimer |
| 6,690,972 B2 | 2/2004 | Conley et al. |
| 6,694,162 B2 | 2/2004 | Hartlep |
| 6,694,163 B1 | 2/2004 | Vining |
| 6,748,098 B1 | 6/2004 | Rosenfeld |
| 6,788,969 B2 | 9/2004 | Dupree et al. |
| 6,827,681 B2 | 12/2004 | Tanner et al. |
| 6,830,544 B2 | 12/2004 | Tanner |
| 6,909,913 B2 | 6/2005 | Vining |
| 7,003,349 B1 | 2/2006 | Andersson et al. |
| 7,008,370 B2 | 3/2006 | Tanner et al. |
| 7,035,690 B2 | 4/2006 | Goetz |
| 7,043,293 B1 | 5/2006 | Baura |
| 7,050,857 B2 | 5/2006 | Samuelsson et al. |
| 7,107,102 B2 | 9/2006 | Daignault, Jr. et al. |
| 7,136,518 B2 | 11/2006 | Griffin et al. |
| 7,136,695 B2 | 11/2006 | Pless et al. |
| 7,146,219 B2 | 12/2006 | Sieracki et al. |
| 7,146,223 B1 | 12/2006 | King |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,216,000 B2 | 5/2007 | Sieracki et al. |
| 7,218,968 B2 | 5/2007 | Condie et al. |
| 7,231,254 B2 | 6/2007 | DiLorenzo |
| 7,239,910 B2 | 7/2007 | Tanner |
| 7,239,926 B2 | 7/2007 | Goetz |
| 7,252,090 B2 | 8/2007 | Goetz |
| 7,257,447 B2 | 8/2007 | Cates et al. |
| 7,266,412 B2 | 9/2007 | Stypulkowski |
| 7,324,851 B1 | 1/2008 | DiLorenzo |
| 7,388,974 B2 | 6/2008 | Yanagita |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,603,177 B2 | 10/2009 | Sieracki et al. |
| 7,617,002 B2 | 11/2009 | Goetz |
| 7,623,918 B2 | 11/2009 | Goetz |
| 7,657,319 B2 | 2/2010 | Goetz et al. |
| 7,676,273 B2 | 3/2010 | Goetz et al. |
| 2002/0062143 A1 | 5/2002 | Baudino et al. |
| 2002/0123780 A1 | 9/2002 | Grill et al. |
| 2002/0128694 A1 | 9/2002 | Holsheimer |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0106916 A1 | 6/2004 | Quaid et al. |
| 2004/0199216 A1 | 10/2004 | Lee et al. |
| 2004/0267330 A1 | 12/2004 | Lee et al. |
| 2005/0033380 A1 | 2/2005 | Tanner et al. |
| 2005/0070781 A1 | 3/2005 | Dawant et al. |
| 2005/0085714 A1 | 4/2005 | Foley et al. |
| 2005/0267347 A1 | 12/2005 | Oster |
| 2006/0017749 A1 | 1/2006 | McIntyre et al. |
| 2006/0020292 A1 | 1/2006 | Goetz et al. |
| 2006/0235472 A1 | 10/2006 | Goetz et al. |
| 2006/0259079 A1 | 11/2006 | King |
| 2007/0049817 A1 | 3/2007 | Preiss et al. |
| 2007/0083104 A1* | 4/2007 | Butson et al. ............ 600/407 |
| 2007/0123953 A1 | 5/2007 | Lee et al. |
| 2007/0156186 A1 | 7/2007 | Lee et al. |
| 2007/0162086 A1 | 7/2007 | DiLorenzo |
| 2007/0185544 A1 | 8/2007 | Dawant et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0276441 A1 | 11/2007 | Goetz |
| 2007/0282189 A1 | 12/2007 | Dan et al. |
| 2008/0027514 A1 | 1/2008 | DeMulling et al. |
| 2008/0081982 A1 | 4/2008 | Simon et al. |
| 2008/0103533 A1 | 5/2008 | Patel et al. |
| 2008/0123922 A1 | 5/2008 | Gielen et al. |
| 2008/0141217 A1 | 6/2008 | Goetz et al. |
| 2008/0154340 A1 | 6/2008 | Goetz et al. |
| 2008/0163097 A1 | 7/2008 | Goetz et al. |
| 2008/0183256 A1 | 7/2008 | Keacher |
| 2008/0215118 A1 | 9/2008 | Goetz et al. |
| 2008/0269588 A1 | 10/2008 | Csavoy et al. |
| 2009/0112289 A1 | 4/2009 | Lee et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010646 A1 | 1/2010 | Drew et al. |
| 2010/0049280 A1 | 2/2010 | Goetz |

OTHER PUBLICATIONS

Butson, Christopher R., et al., "Patient-specific analysis of the volume of tissue activated during deep brain stimulation," NeuroImage, vol. 34, (2007), pp. 661-670.

Butson, C.R., et al., "Role of electrode design on the volume of tissue activated during deep brain stimulation," J Neural Eng., 3(1), (Mar. 2006), pp. 1-8.

Butson et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.

Butson et al., "Current steering to control the volume of tissue activated during deep brain stimulation," vol. 1, No. 1, Dec. 3, 2007, pp. 7-15.

McIntyre, et al., "Computational analysis of deep brain stimulation," Expert Review of Medical Devices, vol. 4, No. 5, Sep. 1, 2007, pp. 615-622, London, GB.

Miranda P. et al., The Electric Field Induced in the Brain by Magnetic Stimulation: a 3-D Finite-Element Analysis of the Effect of Tissue Heterogeneity and Anisotropy, IEEE Transactions on Biomedical Engineering, 50(9): pp. 1074-1085. Sep. 2003.

(56) References Cited

OTHER PUBLICATIONS

Miranda P. et al., "The distribution of currents induced in the brain by Magnetic Stimulation: a finite element analysis incorporating DT-MRI-derived conductivity data," Proc. Intl. Soc. Mag. Reson. Med. vol. 9 (2001), pp. 1540.

Da Silva et al, "A primer on diffusion tensor imaging of anatomical substructures," Neurosurg. Focus 15(1): pp. 1-4. Article 4, 2003.

Dawant, B.M., et al., "Computerized atlas-guided positioning of deep brain stimulators: a feasibility study," Biomedical Image registration, Second International Workshop, WBIR 2003, Revised Papers (Lecture notes in Comput. Sci. vol. 2717, Springer-Verlag Berlin, Germany, (2003), pp. 142-150.

Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.

Mcintyre, C. C., et al., "Electric Field and Stimulating Influence generated by Deep Brain Stimulation of the Subthalamaic Nucleus," Clinical Neurophyssiology vol. 115 (3), International Federation of Clinical Neurophysiology, published by Elsevier Ireland Ltd. (Mar. 2004), pp. 589-595.

Mcintyre, C.C., et al., "Model-based Analysis of deep brain stimulation of the thalamus," Proceedings of the Second joint EMBS/BMES Conference, vol. 3, Annual Fall Meeting of the Biomedical Engineering Society (Cat. No. 02CH37392) IEEE Piscataway, NJ (2002), pp. 2047-2048.

Micheli-Tzanakou, E., et al., "Computational Intelligence for target assessment in Parkinson's disease," Proceedings of SPIE vol. 4479, Applications and Science of Neural Networks, Fuzzy Systems, and Evolutionary Computation IV, (2001), pp. 54-69.

"Deep-brain stimulation of the subthalamic nucleus or the pars interna of the globus pallidus in Parkinson's disease," N. Engl. J. Med., 345(13), Author: Deep-Brain Stimulation for Parkinson's Disease Study Group (Sep. 27, 2001), pp. 956-963.

International Search Report and Written Opinion for Application No. PCT/US2005/023672, dated Jan. 20, 2006, 19 pages.

Adler, D.E., et al., "The tentorial notch: anatomical variation, morphometric analysis, and classification in 100 human autopsy cases," J. Neurosurg. 96(6), (Jun. 2002), pp. 1103-1112.

Alexander, D.C., et al., "Spatial transformations of diffusion tensor magnetic resonance images," IEEE Transactions on Medical Imaging, 20(11), (2001), pp. 1131-1139.

Alo, K.M., et al., "New trends in neuromodulation for the management of neuropathic pain," Neurosurgery, 50(4), (Apr. 2002), 690-703; discussion, pp. 703-704.

Ashby, P., et al., "Neurophysiological effects of stimulation through electrodes in the human subthalamic nucleus," Brain, 122 (Pt 10), (Oct. 1999), pp. 1919-1931.

Baker, K.B., et al., "Subthalamic nucleus deep brain stimulus evoked potentials: Physiological and therapeutic implications," Movement Disorders, 17(5), (Sep./Oct. 2002), pp. 969-983.

Bammer, R., et al., "Diffusion tensor imaging using single-shot SENSE-EPI," Magn, Reson, Med., 48(1), 48(1), (Jul. 2002), pp. 128-136.

Basser, P.J., et al., "MR diffusion tensor spectroscopy and imaging," Biophys. J., 66(1), (Jan. 1994), pp. 259-267.

Basser, P.J., et al., "New currents in electrical stimulation of excitable tissues," Annu. Rev. Biomed. Eng., 2, (2000), pp. 377-397.

Benabid, A.L., et al., "Chronic electrical stimulation of the ventralis intermedius nucleus of the thalamus as a treatment of movement disorders," J. Neurosurg., 84(2), (Feb. 1996), 203-214.

Benabid, A.L., et al., "Combined (thalamotoy and stimulation) stereotactic surgery of the VIM thalamic nucleus for bilateral Parkinson disease," Appl. Neurophysiol., vol. 50, (1987), pp. 344-346.

Benabid, A.L., et al., "Long-term suppression of tremor by chronic stimulation of the ventral intermediate thalamic nucleus," Lancet, 337(8738), (Feb. 16, 1991), 403-406.

Christensen, Gary E., et al., "Volumetric transformation of brain anatomy," IEEE Transactions on Medical Imaging, 16 (6), (Dec. 1997), pp. 864-877.

Cooper, S., et al., "Differential effects of thalamic stimulation parameters on tremor and paresthesias in essential tremor," Movement Disorders, 17(Supp. 5), (2002), S193 (1 page).

Coubes, P., et al., "Treatment of DYT1-generalised dystonia by stimulation of the internal globus pallidus," Lancet, 355 (9222), (Jun. 24, 2000), pp. 2220-2221.

Finnis, K.W., et al., "3-D functional atlas of subcortical structures for image guided stereotactic neurosurgery," Neuroimage, vol. 9, No. 6, Iss. 2, (1999), pp. 758-767.

Finnis, K.W., et al., "3D Functional Database of Subcortical Structures for Surgical Guidance in Image Guided Stereotactic Neurosurgery," Medical Image Computing and Computer-Assisted Intervention—MICCAI '99, Second International Conference, Cambridge, UK, Sep. 19-22, 1999, Proceedings, (1999), pp. 758-767.

Finnis, K.W., et al., "a 3-Dimensional Database of Deep Brain Functional Anatomy, and its Application to Image-Guided Neurosurgery," Proceedings of the Third International Conference on Medical Image Computing and Computer-Assisted Intervention, Lecture Notes In Computer Science, vol. 1935, (2000), pp. 1-8.

Finnis, K.W., et al., "A functional database for guidance of surgical and therapeutic procedures in the deep brain," Proceedings of the 22nd Annual International Conference of the IEEE Engineering in Medicine and Biology Society, vol. 3, (2000), pp. 1787-1789.

Finnis, K.W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part II, Lecture Notes In Computer Science, vol. 2489, (2002), pp. 69-76.

Finnis, K.W., et al., "Subcortical physiology deformed into a patient-specific brain atlas for image-guided stereotaxy," Proceedings of SPIE—vol. 4681 Medical Imaging 2002: Visualization, Image-Guided Procedures, and Display, (May 2002), pp. 184-195.

Finnis, Kirk W., et al., "Three-Dimensional Database of Subcortical Electrophysiology for Image-Guided Stereotatic Functional Neurosurgery," IEEE Transactions on Medical Imaging, 22(1), (Jan. 2003), pp. 93-104.

Gabriels, L., et al., "Deep brain stimulation for treatment-refractory obsessive-compulsive disorder: psychopathological and neuropsychological outcome in three cases," Acta Psychiatr Scand., 107(4), (2003), pp. 275-282.

Gabriels, L.A., et al., "Long-term electrical capsular stimulation in patients with obsessive-compulsive disorder," Neurosurgery, 52(6), (Jun. 2003), pp. 1263-1274.

Goodall, E.V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3), (Sep. 1995), pp. 272-282.

Goodall E.V., et al., "Position-selective activation of peripheral nerve fibers with a cuff electrode," IEEE Transactions on Biomedical Engineering, 43(8), (Aug. 1996), pp. 851-856.

Goodall, E.V., et al., "Simulation of activation and propagation delay during tripolar neural stimulation," Proceedings of the 15th Annual International Conference of the IEEE Engineering in Medicine and Biology Society, (1993), pp. 1203-1204.

Grill, W.M., "Modeling the effects of electric fields on nerve fibers: influence of tissue electrical properties," IEEE Transactions on Biomedical Engineering, 46(8), (1999), pp. 918-928.

Grill, W.M., et al., "Neural and connective tissue response to long-term implantation of multiple contact nerve cuff electrodes," J. Biomed. Mater Res., 50(2), (May 2000), pp. 215-226.

Grill, W.M., "Neural modeling in neuromuscular and rehabilitation research," Proceedings of the 23rd Annual International Conference of the IEEE Engineering in Medicine and Biology Society, vol. 4, (2001), pp. 4065-4068.

Grill, W.M., "Non-invasive measurement of the input-output properties of peripheral nerve stimulating electrodes," Journal of Neuroscience Methods, 65(1), (Mar. 1996), pp. 43-50.

(56) References Cited

OTHER PUBLICATIONS

Grill, W.M., "Quantification of recruitment properties of multiple contact cuff electrodes," IEEE Transactions on Rehabilitation Engineering, [see also IEEE Trans. on Neural Systems and Rehabilitation], 4(2), (Jun. 1996), pp. 49-62.

Grill, W.M., "Spatially selective activation of peripheral nerve for neuroprosthetic applications," Ph.D, Case Western Reserve University, (1995), 245 pages.

Grill, W.M., "Stability of the input-output properties of chronically implanted multiple contact nerve cuff stimulating electrodes," IEEE Transactions on Rehabilitation Engineering [see also IEEE Trans. on Neural Systems and Rehabilitation], (1998), pp. 364-373.

Grill, W.M., "Stimulus waveforms for selective neural stimulation," IEEE Engineering in Medicine and Biology Magazine, 14(4), (Jul.-Aug. 1995), pp. 375-385.

Grill, W. M., "Temporal stability of nerve cuff electrode recruitment properties," IEEE 17th Annual Conference Engineering in Medicine and Biology Society, vol. 2, (1995), pp. 1089-1090.

Gross, R.E., et al., "Advances in neurostimulation for movement disorders," Neurol. Res., 22(3), (Apr. 2000), pp. 247-258.

Haberler, C., et al., "No tissue damage by chronic deep brain stimulation in Parkinson's disease," Ann. Neurol., 48(3), (Sep. 2000), pp. 372-376.

Hamel, W., et al., "Deep brain stimulation of the subthalamic nucleus in Parkinson's disease: evaluation of active electrode contacts," J. Neurol. Neurosurg. Psychiatry, 74(8), (Aug. 2003), pp. 1036-1046.

Haueisen, J., et al., "The influence of brain tissue anisotropy on human EEG and MEG," Neuroimage, 15(1), (Jan. 2002), pp. 159-166.

Hodaie, M., et al., "Chronic anterior thalamus stimulation for intractable epilepsy," Epilepsia, 43(6), (Jun. 2002), pp. 603-608.

Hoekema, R., et al., "Multigrid solution of the potential field in modeling electrical nerve stimulation," Comput. Biomed. Res., 31(5), (Oct. 1998), pp. 348-362.

Holsheimer, J., et al., "Identification of the target neuronal elements in electrical deep brain stimulation," Eur. J. Neurosci., 12(12), (Dec. 2000), pp. 4573-4577.

Jezernik, S., et al., "Neural network classification of nerve activity recorded in a mixed nerve," Neurol. Res., 23(5), (Jul. 2001), pp. 429-434.

Jones, D.K., et al., "Optimal strategies for measuring diffusion in anisotropic systems by magnetic resonance imaging," Magn. Reson. Med., 42(3), (Sep. 1999), pp. 515-525.

Krack, P., et al., "Postoperative management of subthalamic nucleus stimulation for Parkinson's disease," Mov. Disord., vol. 17(suppl. 3), (2002), pp. 188-197.

Le Bihan, D., et al., "Diffusion tensor imaging: concepts and applications," J. Magn. Reson. Imaging, 13(4), (Apr. 2001), pp. 534-546.

Lee, D.C., et al., "Extracellular electrical stimulation of central neurons: quantitative studies," In: Handbook of neuroprosthetic methods, WE Finn and PG Lopresti (eds) CRC Press, (2003), 95-125.

Levy, A. L., et al., "An Internet-connected, patient-specific, deformable brain atlas integrated into a surgical navigation system," J. Digit. Imaging, 10(3 Suppl 1), (Aug. 1997), pp. 231-237.

McIntyre, Cameron C., et al., "Cellular effects of deep brain stimulation model-based analysis of activation and inhibition," J. Neurophysiol., 91(4), (Apr. 2004), pp. 1457-1469.

McIntyre, Cameron C., et al., "Electric field generated by deep brain stimulation of the subthalamic nucleus," Biomedical Engineering Society Annual Meeting, Nashville TN, (Oct. 2003), 16 pages.

McIntyre, Cameron C., et al., "Extracellular stimulation of central neurons: influence of stimulus waveform and frequency on neuronal output," J. Neurophysiol., 88(4), (Oct. 2002), pp. 1592-1604.

McIntyre, C. C., et al., "Microstimulation of spinal motoneurons: a model study," Proceedings of the 19th Annual International Conference of the IEEE Engineering in Medicine and Biology society, vol. 5, (1997), 2032-2034.

McIntyre, C. C., et al., "Model-based design of stimulus trains for selective microstimulation of targeted neuronal populations," Proceedings of the 23rd Annual International Conference of the IEEE Engineering in Medicine and Biology Society, vol. 1, (2001), pp. 806-809.

McIntyre, C. C., et al., "Model-based design of stimulus waveforms for selective microstimulation in the central nervous system," Proceedings of the First Joint [Engineering in Medicine and Biology, 1999. 21st Annual Conf. and the 1999 Annual FallMeeting of the Biomedical Engineering Soc. BMES/EMBS Conference, vol. 1, (1999), 384 (1 page).

McIntyre, Cameron C., et al., "Modeling the excitability of mammalian nerve fibers: influence of afterpotentials on the recovery cycle," J. Neurophysiol., 87(2), (Feb. 2002), pp. 995-1006.

McIntyre, Cameron C., et al., "Selective microstimulation of central nervous system neurons," Annals of biomedical engineering, 28(3), (Mar. 2000), pp. 219-233.

McIntyre, C. C., et al., "Sensitivity analysis of a model of mammalian neural membrane," Biol. Cybern., 79(1), (Jul. 1998), pp. 29-37.

McIntyre, Cameron C., et al., "Uncovering the mechanism(s) of action of deep brain stimulation: activation, inhibition, or both," Clin. Neurophysiol., 115(6), (Jun. 2004), pp. 1239-1248.

McIntyre, Cameron C., et al., "Uncovering the mechanism(s) of deep brain stimulation for Parkinson's disease through functional imaging, neural recording, and neural modeling," Crit. Rev. Biomed. Eng., 30(4-6), (2002), pp. 249-281.

McNeal, D. R., et al., "Analysis of a model for excitation of myelinated nerve," IEEE Trans Biomed Eng., vol. 23, (1976), pp. 329-337.

Miocinovic, S., et al., "Sensitivity of temporal excitation properties to the neuronal element activated by extracellular stimulation," J. Neurosci. Methods, 132(1), (Jan. 15, 2004), pp. 91-99.

Moffitt, M. A., et al., "Prediction of myelinated nerve fiber stimulation thresholds: limitations of linear models," IEEE Transactions on Biomedical Engineering, 51(2), (2003), pp. 229-236.

Moro, E., et al., "The impact on Parkinson's disease of electrical parameter settings in STN stimulation," Neurology, 59 (5), (Sep. 10, 2002), pp. 706-713.

Nowak, L.G., et al., "Axons, but not cell bodies, are activated by electrical stimulation in cortical gray matter, I. Evidence from chronaxie measurements," Exp. Brain Res., 118(4), (Feb. 1998), pp. 477-488.

Nowak, L.G., et al., "Axons, but not cell bodies, are activated by electrical stimulation in cortical gray matter, II. Evidence from selective inactivation of cell bodies and axon initial segments," Exp. Brain Res., 118(4), (Feb. 1998), pp. 489-500.

O'Suilleabhain, P.E., et al., "Tremor response to polarity, voltage, pulsewidth and frequency of thalamic stimulation" Neurology, 60(5), (Mar. 11, 2003), pp. 786-790.

Pierpaoli, C., et al., "Toward a quantitative assessment of diffusion anisotropy," Magn. Reson. Med., 36(6), (Dec. 1996), pp. 893-906.

Plonsey, R., et al., "Considerations of quasi-stationarity in electrophysiological systems," Bull Math Biophys., 29(4), (Dec. 1967), pp. 657-664.

Ranck, J.B., "Specific impedance of rabbit cerebral cortex," Exp. Neurol., vol. 7, (Feb. 1963), pp. 144-152.

Ranck, J.B., "The Specific impedance of the dorsal columns of the cat: an anisotropic medium," Exp. Neurol., 11, (Apr. 1965), pp. 451-463.

Ranck, J.B., "Which elements are excited in electrical stimulation of mammalian central nervous system: a review," Brain Res., 98(3), (Nov. 21, 1975), pp. 417-440.

Rattay, F., et al., "A model of the electrically excited human cochlear neuron, I. Contribution of neural substructures to the generation and propagation of spikes," Hear Res., 153(1-2), (Mar. 2001), pp. 43-63.

Rattay, F., "A model of the electrically excited human cochlear neuron, II. Influence of the three-dimensional cochlear structure on neural excitability," Hear Res., 153(1-2), (Mar. 2001), pp. 64-79.

Rattay, F., "Arrival at Functional Electrostimulation by modelling of fiber excitation," Proceedings of the Ninth annual Conference of the IEEE Engineering in Medicine and Biology Society, (1987), pp. 1459-1460.

Rattay, F., "The influence of intrinsic noise can preserve the temporal fine structure of speech signals in models of electrically stimulated

(56) References Cited

OTHER PUBLICATIONS human cochlear neurones," Journal of Physiology, Scientific Meeting of the Physiological Society, London, England, UK Apr. 19-21, 1999, (Jul. 1999), 170P (1 page).

Rizzone, M., et al., "Deep brain stimulation of the subthalamic nucleus in Parkinson's disease: effects of variation in stimulation parameters," J. Neurol. Neurosurg. Psychiatry., 71(2), (Aug. 2001), pp. 215-219.

Saint-Cyr, J.A., et al., "Localization of clinically effective stimulating electrodes in the human subthalamic nucleus on magnetic resonance imaging," J. Neurosurg., 87(5), (Nov. 2002), pp. 1152-1166.

Sances, A., et al., "In Electroanesthesia: Biomedical and Biophysical Studies," A Sances and SJ Larson, Eds., Academic Press, NY, (1975), pp. 114-124.

St. Jean, P., et al., "Automated atlas integration and interactive three-dimensional visualization tools for planning and guidance in functional neurosurgery," IEEE Transactions on Medical Imaging, 17(5), (1998), pp. 672-680.

Starr, P.A., et al., "Implantation of deep brain stimulators into the subthalamic nucleus: technical approach and magnetic resonance imaging-verified lead locations," J. Neurosurg., 97(2), (Aug. 2002), pp. 370-387.

Sterio, D., et al., "Neurophysiological refinement of subthalamic nucleus targeting," Neurosurgery, 50(1), (Jan. 2002), pp. 58-69.

Struijk, J.J., et al., "Excitation of dorsal root fibers in spinal cord stimulation: a theoretical study," IEEE Transactions on Biomedical Engineering, 40(7), (Jul. 1993), pp. 632-639.

Struijk, J.J., et al., "Recruitment of dorsal column fibers in spinal cord stimulation: influence of collateral branching," IEEE Transactions on Biomedical Engineering, 39(9), (Sep. 1992), pp. 903-912.

Tamma, F., et al., "Anatomo-clinical correlation of intraoperative stimulation-induced side-effects during HF-DBS of the subthalamic nucleus," Neurol. Sci., vol. 23 (Suppl. 2), (2002), pp. 109-110.

Tarler, M., et al., "Comparison between monopolar and tripolar configurations in chronically implanted nerve cuff electrodes," IEEE 17th Annual Conference Engineering in Medicine and Biology Society, vol. 2, (1995), pp. 1093-1094.

Testerman, Roy L., "Cortical response to callosal stimulation: A model for determining safe and efficient stimulus parameters," Annals of Biomedical Engineering, 6(4), (1978), pp. 438-452.

Tuch, D. S., et al., "Conductivity mapping of biological tissue using diffusion MRI," Ann. NY Acad. Sci., 888, (Oct. 30, 1999), pp. 314-316.

Tuch, D. S., et al., "Conductivity tensor mapping of the human brain using diffusion tensor MRI," Proc. Natl. Acad. Sci. USA, 98(20), (Sep. 25, 2001), pp. 11697-11701.

Veraart, C., et al., "Selective control of muscle activation with a multipolar nerve cuff electrode," IEEE Transactions on Biomedical Engineering, 40(7), (Jul. 1993), pp. 640-653.

Vercueil, L., et al., "Deep brain stimulation in the treatment of severe dystonia," J. Neurol., 248(8), (Aug. 2001), pp. 695-700.

Vitek, J. L., "Mechanisms of deep brain stimulation: excitation or inhibition," Mov. Disord., vol. 17 (Suppl. 3), (2002), pp. S69-S72.

Voges, J., et al., "Bilateral high-frequency stimulation in the subthalamic nucleus for the treatment of Parkinson disease: correlation of therapeutic effect with anatomical electrode position," J. Neurosurg., 96(2), (Feb. 2002), pp. 269-279.

Volkmann, J., et al., "Introduction to the programming of deep brain stimulators," Mov. Disord., vol. 17 (Suppl. 3), pp. (2002), S181-S187.

Wakana, S., et al., "Fiber tract-based atlas of human white matter anatomy," Radiology, 230(1), (Jan. 2004), pp. 77-87.

Warman, E.N., et al., "Modeling the effects of electric fields on nerve fibers: Determination of excitation thresholds," IEEE Transactions on Biomedical Engineering, 39(12), (1992), pp. 1244-1254.

Wu, Y.R., et al., "Does Stimulation of the GPi control dyskinesia by activating inhibitory axons?," Mov. Disord., vol. 16, (2001), pp. 208-216.

Yelnik, J., et al., "Localization of stimulating electrodes in patients with Parkinson disease by using a three-dimensional atlas-magnetic resonance imaging coregistration method," J. Neurosurg., 99(1), (Jul. 2003), pp. 89-99.

Yianni, John, et al., "Globus pallidus internus deep brain stimulation for dystonic conditions: a prospective audit," Mov. Disord., vol. 18, (2003), pp. 436-442.

Zonenshayn, M., et al., "Comparison of anatomic and neurophysiological methods for subthalamic nucleus targeting," Neurosurgery, 47(2), (Aug. 2000), pp. 282-294.

Guridi et al. "The subthalamic nucleus, hemiballismus and Parkinson's disease: reappraisal of a neurological dogma," Brain, vol. 124, 2001, pp. 5-19.

Hanekom, "Modelling encapsulation tissue around cochlear implant electrodes," Med. Biol. Eng. Comput. vol. 43 (2005), pp. 47-55.

\* cited by examiner

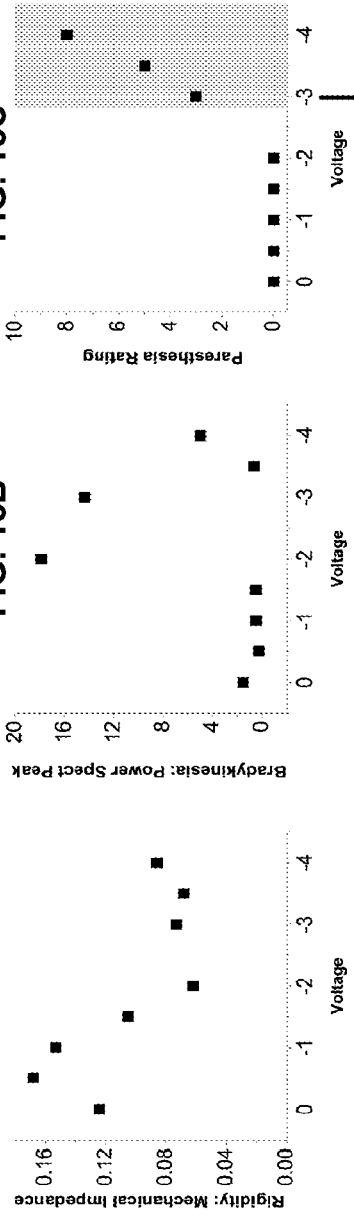

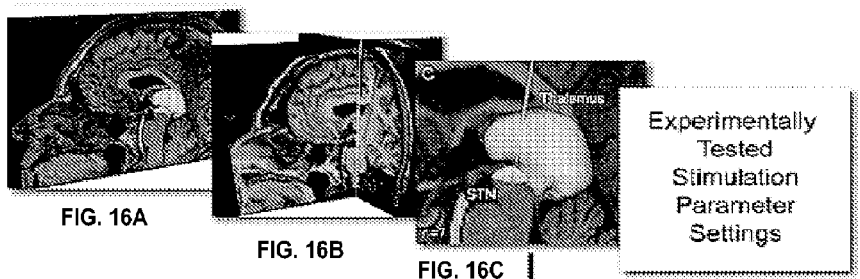
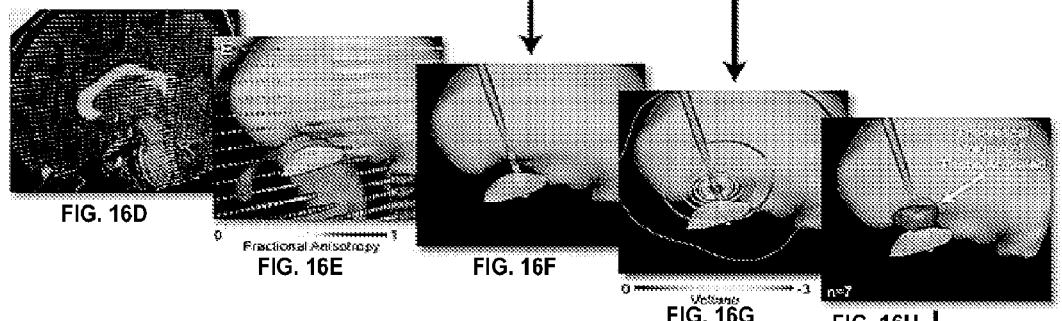
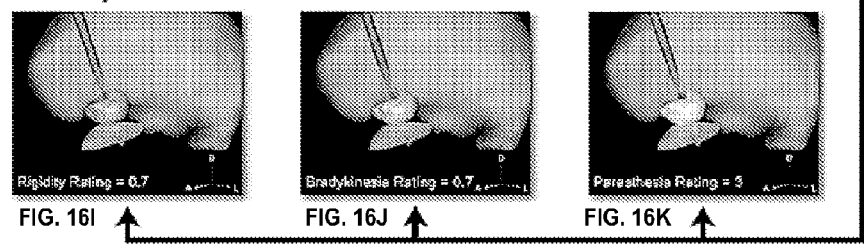

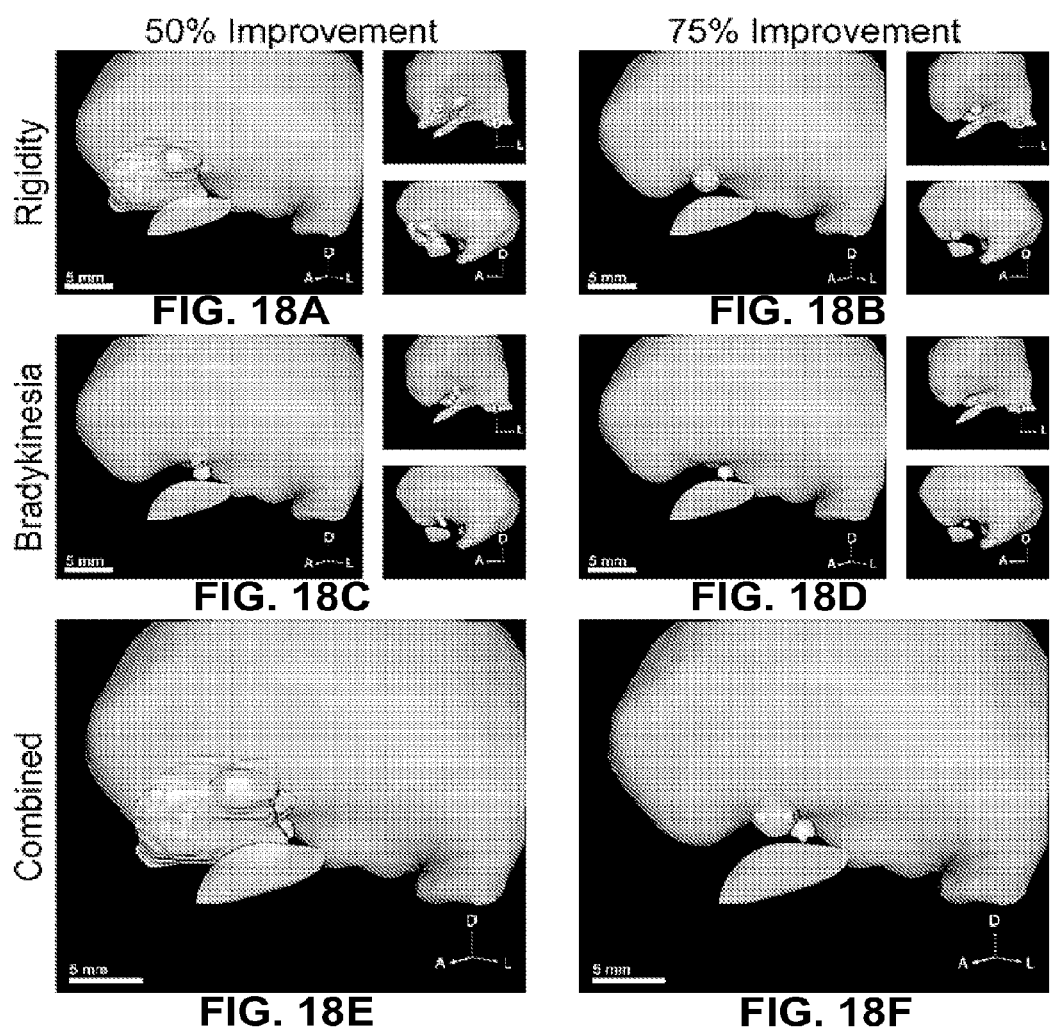

| Patient | Sex | Primary Symptoms | Age at exp | Years post-surg. | Hemi-sphere | Contact | | 0 | 1 | 2 | 3 | Number of VTAs |
|---|---|---|---|---|---|---|---|---|---|---|---|---|
| 1 | M | Bradykinesia, rigidity | 49 | 1.9 | Left | Imp | | >2000 | >2000 | >2000 | 1676 | 33 |
| | | | | | | V | | 0 to -4 | 0 to -4 | 0 to -4 | 0 to -4.5 | |
| 2 | M | gait, freezing, bradykinesia | 61 | 2.5 | Right | Imp | | 1559 | 1315 | 1468 | 1321 | 18 |
| | | | | | | V | | 0 to -2 | 0 to -2 | 0 to -2.5 | 0 to -2.5 | |
| 3 | M | tremor, freezing, balance | 63 | 4.1 | Right | Imp | | >2000 | 1681 | >2000 | 997 | 13 |
| | | | | | | V | | 0 to -2 | 0 to -3 | 0 to -4 | 0 to -4 | |
| 4 | M | rigidity, bradykinesia | 65 | 2.1 | Left | Imp | | 1041 | 1036 | 1086 | 1249 | 12 |
| | | | | | | V | | 0 to -1 | 0 to -3 | 0 to -4 | 0 to -4 | |
| 5 | M | rigidity, bradykinesia, tremor | 59 | 0.5 | Left | Imp | | 906 | 984 | 890 | 871 | 21 |
| | | | | | | V | | 0 to -5 | 0 to -5 | 0 to -6 | 0 to -5 | |
| 6 | M | rigidity, bradykinesia, tremor | 72 | 1.1 | Left | Imp | | 1912 | 1387 | 1315 | 1462 | 25 |
| | | | | | | V | | 0 to -4 | 0 to -5 | 0 to -7 | 0 to -9 | |
| | M | freezing, dyskinesias, tremor | | | Left | Imp | | 1669 | 1475 | 1315 | 1255 | 41 |
| | | | | | | V | | 0 to -4.5 | 0 to -5 | 0 to -10 | 0 to -10 | 163 |

FIG. 19

| Patient | Sex | Pain Locations | Age at exp | Years post-surg. | | Contact 0 | 1 | 2 | 3 | Number of VTAs |
|---|---|---|---|---|---|---|---|---|---|---|
| 1 | M | Lower Back | 49 | 1.9 | Imp | >2000 | >2000 | >2000 | 1676 | |
| | | | | | V | 0 to -4 | 0 to -4.5 | 0 to -4 | 0 to -4.5 | 33 |
| | | Right Knee | | | Imp | 1559 | 1315 | 1468 | 1321 | |
| | | | | | V | 0 to -2 | 0 to -2 | 0 to -2.5 | 0 to -2.5 | 19 |
| 2 | M | Left Abdominal | 51 | 2.5 | Imp | >2000 | 1681 | >2000 | 997 | |
| | | | | | V | 0 to -2 | 0 to -3 | 0 to -4 | 0 to -4 | 13 |
| 3 | M | Lower Back | 63 | 4.1 | Imp | 1041 | 1036 | 1086 | 1249 | |
| | | | | | V | 0 to -1 | 0 to -3 | 0 to -4 | 0 to -4 | 12 |
| 4 | M | Right Thigh | 65 | 2.1 | Imp | 906 | 984 | 890 | 871 | |
| | | | | | V | 0 to -5 | 0 to -5 | 0 to -6 | 0 to -5 | 21 |
| 5 | M | Left Lower Back | 59 | 0.5 | Imp | 1912 | 1387 | 1315 | 1462 | |
| | | | | | V | 0 to -4 | 0 to -5 | 0 to -7 | 0 to -9 | 25 |
| 6 | M | Left Knee | 72 | 1.1 | Imp | 1669 | 1475 | 1315 | 1255 | |
| | | | | | V | 0 to -4.5 | 0 to -5 | 0 to -10 | 0 to -10 | 41 |
| | | | | | | | | | | 163 |

FIG. 27

SYSTEM AND METHOD TO DEFINE TARGET VOLUME FOR STIMULATION OF THE SPINAL CORD AND PERIPHERAL NERVES

CROSS-REFERENCE TO RELATED APPLICATIONS

This application is a continuation of U.S. patent application Ser. No. 12/881,903, filed on Sep. 14, 2010, now U.S. Pat. No. 8,594,800 which is a continuation-in-part of PCT/US2009/066821, filed on Dec. 4, 2009, which claims the benefit of U.S. Provisional Patent Application No. 61/120,006, filed on Dec. 4, 2008, and entitled SYSTEM AND METHOD TO DEFINE TARGET VOLUME FOR STIMULATION IN BRAIN. This application is also a continuation-in-part of U.S. patent application Ser. No. 13/480,858, filed on May 25, 2012, now U.S. Pat. No. 8,538,543 which is a divisional of related to U.S. patent application Ser. No. 11/606,260, now U.S. Pat. No. 8,209,027, filed on Nov. 28, 2006, and entitled SYSTEM AND METHOD TO DESIGN STRUCTURE FOR DELIVERING ELECTRICAL ENERGY TO TISSUE, which claims the benefit of U.S. provisional patent application No. 60/740,031 filed on Nov. 28, 2005, and entitled ROLE OF ELECTRODE DESIGN ON THE VOLUME OF TISSUE ACTIVATED DURING DEEP BRAIN STIMULATION. The entire contents of each of the above-identified applications are incorporated herein by reference.

GOVERNMENT FUNDING

This invention was made with government support under Grant Nos. NIH R01 NS-059736 and NIH F32 NS-52042. The U.S. government has certain rights in the invention.

TECHNICAL FIELD

The present invention relates generally to systems and methods for determining a target volume for stimulation of a patient's neural tissue, such as the brain, spinal cord or a peripheral nerve.

BACKGROUND

Electrical stimulation of the nervous system has provided a therapeutic treatment for a variety of disorders. For example, electrical stimulation has been applied to pain management, such as by performing stimulation of the spinal cord. Electrical stimulation has been performed to augment hearing in the context of cochlear implants. Deep brain stimulation (DBS) has also become an established therapy for treating various conditions including, for example, Parkinson's disease and dystonia. DBS has also been employed to treat several other conditions, such as clinical depression, obsessive compulsive disorder, and epilepsy to name a few.

By way of further example, the discovery that high frequency DBS generates clinical benefits analogous to those achieved by surgical lesioning has transformed the use of functional neurosurgery for the treatment of movement disorders. In first world countries, thalamic DBS for intractable tremor has replaced ablative lesions of the thalamus, and DBS of the subthalamic nucleus or globus pallidus internus (GPi). GPi has replaced pallidotomy in the treatment of the cardinal motor features of Parkinson's disease (e.g., tremor, rigidity, bradykinesia). GPi DBS has also emerged as an effective therapy for dystonia, and the utility of DBS is being examined for the treatment of epilepsy, obsessive-compulsive disorder, Tourette's syndrome, and major depression.

Despite the documented clinical successes of neurostimulation, the mechanisms and effects of neurostimulation at the neuronal level remain difficult to predict. As a result, modeling and simulation have played increasingly important roles in the engineering design and scientific analysis of neurostimulation.

SUMMARY

The invention relates generally to systems and methods for determining a target volume for stimulation of a patient's neural tissue, such as the brain, spinal cord or peripheral nerves.

One embodiment provides a computer-implemented method that includes storing (e.g., in memory) a volume of tissue activation (VTA) data structure that is derived from analysis of a plurality of patients. Patient data is received for a given patient, the patient data representing an assessment of a patient condition. The VTA data structure is evaluated relative to the patient data to determine a target VTA for achieving a desired therapeutic effect for the given patient. For example, the VTA data structure can be embodied as a statistical atlas of the brain, spinal cord or other neural target site that is constructed from anatomical and electrical data acquired for a patient population. The target volume of activation thus can correspond to a statistically optimized volume of tissue that can be stimulated to achieve a desired therapeutic result for the patient.

Another embodiment provides a system for determining a volume of tissue activation for achieving a desired therapeutic effect for a given patient. The system includes a volume of tissue activation (VTA) data structure stored in memory. The VTA data structure (e.g., a statistical atlas of a particular neural tissue such as the brain, spinal cord or a peripheral nerve) is derived from analysis anatomical and electrical data acquired for a plurality of patients. Patient data is also stored in the memory. The patient data representing an assessment of a patient condition for the given patient. A processor is programmed to execute instructions for evaluating the VTA data structure relative to the patient data to determine a target VTA for achieving a desired therapeutic effect for the given patient. The processor is also programmed to determine at least one of a structural parameter and a stimulation parameter that can provide a design VTA for the given patient that substantially matches the target VTA.

Methods can further be implemented to stimulate the patient's neural tissue, such as the brain, spinal cord or a peripheral nerve for the target VTA to achieve a desired therapeutic effect. By way of further example, the methods can be implemented as including a pre-operative phase in which a target point and trajectory are defined for implantation of an electrode structure. The target point and trajectory can be determined based on the target VTA determined for the patient, such as based on a set of patient data. After the electrode has been implanted at the predetermined location, an optimization process can be performed to compute stimulation parameters that provide for a volume of tissue activation that substantially matches the target VTA. The stimulation parameters to achieve the target VTA can be computed, for example, based on electrical properties of the electrode structure, a location of the implanted electrode structure (e.g., in a stereotactic coordinate system for the patient), patient image data and the determined target VTA.

BRIEF DESCRIPTION OF THE DRAWINGS

FIGS. 15A through 15E are graphs of data acquired from clinical evaluation of patients for different stimulation parameters.

FIGS. 16A through 16K depict patient specific stimulation models that can be utilized for constructing a VTA data structure according to an aspect of the invention.

FIGS. 18A through 18F depict examples of clinical outcomes for a plurality of VTAs for different symptoms.

FIG. 19 is a table illustrating an example of sample data that can be utilized for constructing a VTA data structure according to an aspect of the invention.

FIG. 27 is a table illustrating an example of sample data that can be used for constructing a VTA data structure.

DETAILED DESCRIPTION

The invention relates generally to systems and methods for determining a target volume of tissue activation (VTA) for stimulation of a patient's tissue, such as neural tissue.

It will be appreciated that portions of the invention used to determine a target VTA or otherwise utilize the target VTA may be embodied as a method, data processing system, or computer program product. Accordingly, these embodiments of the present invention may take the form of an entirely hardware embodiment, an entirely software embodiment, or an embodiment combining software and hardware, such as shown and described with respect to the computer system of FIG. 20. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, flash storage devices and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other processor-based apparatus provide steps for implementing the functions specified in the block or blocks.

Figure 1:
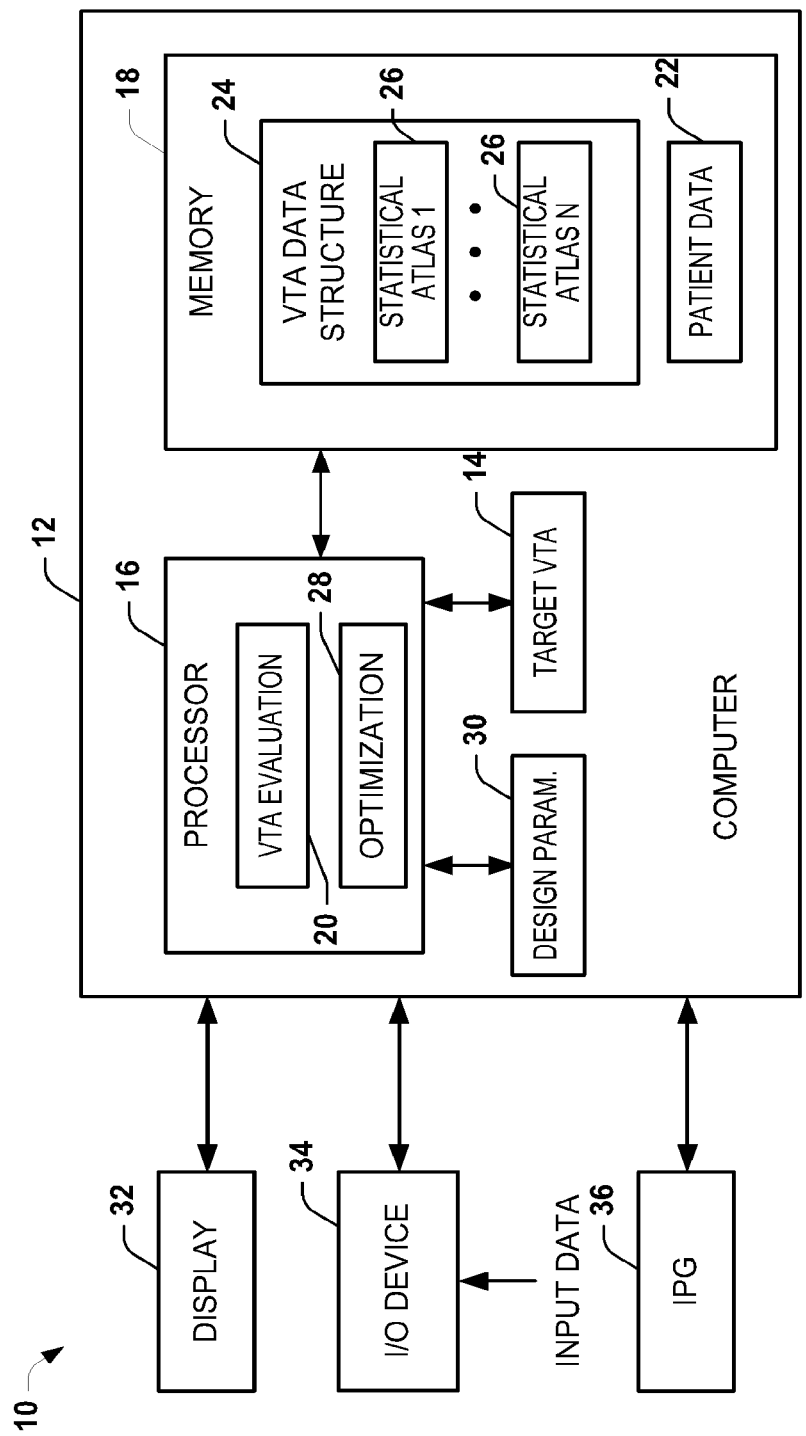
FIG. 1 depicts an example of a system that can be utilized to identify a target volume of tissue activation for a patient.

FIG. 1 depicts an example of a system 10 that can be employed to determine a target VTA. The system 10 is shown as including a computer 12 that employs data and program methods to determine a target VTA 14 for a given patient according to an aspect of the invention. The computer 12 can be a workstation, a standalone computer, a notebook computer, or it can be implemented as part of a microprocessor-based appliance or other equipment available that is programmed based on the teachings contained herein.

The computer 12 includes a processor 16 that executes instructions programmed for performing the methods described herein. The instructions can be stored in associated memory 18. In the example of FIG. 1, the processor 16 is depicted as running a VTA evaluation method 20. The VTA evaluation method 20 can be stored in the memory 18 and loaded into the processor 16 for determining the target VTA 14.

As used herein, a VTA represents an anatomical region of tissue, such as a three-dimensional volume of tissue that includes cells of the nervous system. For example. the tissue can be neural tissue in the brain or other part of the central nervous system, such as the spinal cord. The neural tissue can also be part of the peripheral nervous system such as the somatic and autonomic nervous system. For example, target sites of the peripheral nervous system for which a VOA can be predicted and for which other methods of the present invention can be utilized include cranial nerves (such as, for example, the vagus nerve and/or sacral nerve) and spinal nerves. Target sites in the autonomic nervous system include the sympathetic nervous system and parasympathetic nervous system. Specific sites within these systems include sympathetic or parasympathetic nerves or ganglia.

The target VTA thus corresponds to a region of tissue that if stimulated for a given patient with electrical, chemical or a combination of electrical and chemical stimulation, is expected to achieve a desired therapeutic effect for the given patient. The therapeutic effect can vary according to the condition of the patient being treated. While the phrase "volume of tissue activation," VTA and its variants typically represents a volume of tissue activation of an anatomical region, it will be appreciated that such volume could also represent a volume of inhibition region or a volume of tissue deactivation, as stimulation could result in either generation of an activation potential or the inhibition of existing activation potentials or a combination of activation and inhibition of activation potentials for achieving a desired therapeutic effect.

The VTA evaluation method 20 computes the target VTA based on an analysis of patient-specific data 22 relative to information in a VTA data structure 24. The resulting target VTA 14 can correspond to a probabilistic definition of the anatomical volume in an identified anatomical region. The VTA evaluation method can determine the target VTA 14 from a statistically significant subset of the VTA data structure 24. The relevant subset of the VTA data structure 24 can vary according to the patient data 22, such as can vary depending on an evaluation of the patient's condition.

The patient data 22 can include information corresponding to a clinical assessment of a disease or condition (e.g., identified from a diagnosis) of the patient. The clinical assessment may be determined from a qualitative and/or quantitative assessment of the patient's condition. For example, qualitative assessments can include any clinical rating system, such as the Unified Parkinson's Disease Rating Scale (UPDRS) or other known rating systems for a particular disease. Other qualitative assessments can be patient perceived quality of life or perceptible (by the patient or other person) metric. One example of a quantitative factor includes acceleration of a body part during a tremor, such as can be measured by one or more accelerometers attached to the patient's body during testing.

The type of information used for the patient data 22 can be of the same or similar to the types of information acquired in conjunction with a clinical assessment of the therapeutic effect or a clinical outcome for a plurality of different stimulation parameters can be utilized to construct the VTA data structure 24. It will be understood that the types of information that can be utilized to assess a given patient's condition can vary depending on conventional standards, which further can be tailored according to the patient's condition.

The VTA data structure 24 further can utilize a patient-specific model that can comprise three fundamental components that are co-registered into a single platform: 1) anatomical model, 2) electric field model, and 3) neural activation model. Clinically defined therapeutic and non-therapeutic stimulation parameters can be used to determine VTAs in each given patient. For example, each of a plurality of VTA's can be mapped onto a common atlas neural tissue platform to construct a 3D probabilistic map of overlapping VTAs and their relationship with the surrounding neuroanatomy. The 3D probabilistic maps defined by the VTA data structure 24 can be used to ascertain a target VTA for achieving a desired therapeutic results for a given patient according to the tissue volume determined to provide a statistically maximal clinical benefit based on the input data 22 corresponding to a clinical assessment for the given patient.

The VTA data structure 24 can include data corresponding to a plurality of statistical atlases 26, indicated as STATISTICAL ATLAS 1 through N, where N is a positive integer denoting the number of atlases. As a further example, the VTA data structure 24 can be organized as a hierarchy of atlases 26, such as can be arranged hierarchically or otherwise organized according to specificity of disease and symptoms and therapeutic results associated with stimulation for a plurality of VTAs. Each of the atlases 26 further can be in the form of a statistical representation of data that identifies the likelihood or probability of desirable therapeutic effect associated with providing stimulation for a given VTA, which can vary according to the disease and/or symptoms for each patient in the population from which the atlas has been generated. The atlases 26 can also provide similar statistical information of negative or undesirable therapeutic effects associated with providing stimulation for respective VTAs. The negative or undesirable therapeutic effects can include side effects perceived by a physician or patient during stimulation of a given VTA, such as can be afforded values depending on applicable qualitative and/or quantitative assessments.

As a further example, the VTA for a plurality of different stimulation parameters and electrode placements can be determined according to the systems and methods shown and described in the above-incorporated U.S. Pat. No. 7,346,382. For instance, the anatomical location of an electrode can be determined from an atlas brain or other neural tissue for each patient in the population (e.g., based on a relative location within a stereotactic coordinate system). Based on the location of the electrode or electrodes in the brain or other neural tissue such as the spinal cord or a peripheral nerve and the stimulation parameters (e.g., amplitude, frequency, pulse width), a corresponding VTA can be computed for each of a plurality of different stimulation parameters. Additionally, one or more corresponding VTAs can be computed for each of a plurality of electrode locations, which VTA will vary depending on the stimulation parameters. The results of each such stimulation can also be identified and assigned a therapeutic value or set of values (e.g., a score) that is stored for the patient associated with the electrode location information and the stimulation parameters and the computed VTA data. The VTA data structure can be generated based on respective clinical assessments for a plurality of patients in the representative population.

Similarly to the patient input data 22, the therapeutic results stored for each set of stimulation parameters can include any number of one or more qualitative assessments, quantitative assessments or a combination of qualitative and quantitative assessments. For example, qualitative assessments can include any clinical rating system, such as the UPDRS or other known rating systems for a particular disease. Other qualitative assessments can be patient perceived quality of life or perceptible (by the patient or other person)

metric. The criteria utilized to assess the therapeutic effects during stimulation of a given VTA may be the same or different criteria as is used to assess the patient condition and provide the patient input data.

Those skilled in the art will understand and appreciate various other qualitative and quantitative metrics that can be utilized to assess the therapeutic effect associated with a given set of stimulation parameters. It further will be understood that while the majority of stimulation parameters are described herein as relating to electrical stimulation parameters, stimulation parameters can also be associated with chemical stimulation, such as according to a dosage and application at a particular anatomical site, which chemical stimulation also has a corresponding VTA. Such chemical stimulation parameters and therapeutic results data thus can be used in the VTA data structure 24.

By repeating stimulation of known tissue with different stimulation parameters, a corresponding data set can provide an indication of therapeutic effect (e.g., including positive and/or negative effects) for a plurality of different VTAs. Such information can be acquired for a large sample patient population, which can be analyzed by known statistical methods to provide the resulting VTA data structure. It will be appreciated that the VTA data structure (e.g., the 3D probabilistic maps) can be updated based on clinical data acquired for additional patients, including based on the results of stimulating a patient according to the target VTA 14 determined by the VTA evaluation method 20.

After a target VTA has been determined for a given patient, the processor can be programmed to warp or morph such target VTA to fit the corresponding anatomical region of a particular patient (e.g., based on patient anatomical model determined for the patient) and stored to provide a patient-specific target VTA data 14. For instance, the target VTA can be provided to define a volume of tissue in a generic atlas brain or spinal cord or other neural tissue, which can be mapped to the given patient based on corresponding anatomical data acquired for the given patient via a suitable imaging modality, such as MRI, CT and the like.

The computer system 12 can also include an optimization design algorithm 28 that is programmed to determine a set of electrode design and stimulation parameters 30 which can be employed to stimulate tissue (when implanted at a predetermined location in a given patient) to achieve the target VTA 14. Those skilled in the art will understand and appreciate various optimization methods that can be utilized by the design algorithm 28 to determine the structural parameters and/or the electrical parameters for approximating the target VTA 14, which has been determined to achieve a desired therapeutic effect.

The design algorithm 28 can be performed pre-operatively or intra-operatively or it can be performed both pre-operatively and intra-operatively. For instance, by performing the process pre-operatively a customized electrode design can be selected, which can be selected from a set of commercially available structures or a fully customized patient-specific design can be generated. Then after the implant has been positioned, such as a geometric center of the target VTA, the optimization can be performed to determine the set of stimulation parameters to achieve the target VTA based on the patient data 22, the electrode configuration and the location of the electrode in a stereotactic coordinate system for the patient.

By way of example, volume based optimization algorithms can be applied to the target VTA to define optimal stimulation parameter settings. The clinically defined therapeutic stimulation parameters thus can represent the gold standard. Quantitative measures as well as qualitative measures can be utilized as parameters to determine appropriate optimal settings to achieve the desired therapeutic results. The particular quantitative or qualitative parameters may vary according to the particular symptoms of the patient. For instance, known clinical rating scales can provide quantitative measures for a variety of conditions, including but not limited to bradykinesia, rigidity, tremor, and bimanual hand function. In certain embodiments, the present invention can be used to target specific dermatome areas on the patient where pain or discomfort is being experienced. These dermatome areas correspond physiologically with specific regions of the spinal cord. Thus, the stimulation parameters can be selected to direct stimulation to these regions of the spinal cord to affect that particular dermatome area(s).

As a further example, in some cases it may be sufficient to ascertain the structural parameter(s) over a predefined set of stimulation parameters during a first optimization routine. The stimulation parameters 30 can be fine tuned during a second optimization routine. Alternatively, the structural parameters and the electrical parameters can form a parameter space that is optimized collectively. The order and interrelationship between the stimulation parameters and the structural parameters thus can be optimized to achieve or approximate a desired therapeutic effect to varying degrees of specificity and according to what approximations and assumptions are made during such analysis. Additionally, the resulting parameters 30 can be determined to accommodate anatomical variability between patients as well as potential surgical variability associated with implantation of the electrode to a target implantation site. The electrode design parameters 30 further can be ascertained to provide electrode contact dimensions that maximize the stimulation influence while keeping charge injection levels to a minimum.

The design parameters 30 computed by the design algorithm 28 can include electrode structural (or morphological) parameters, electrode stimulation parameters or a combination of structural and stimulation parameters. For the example of an electrode having a cylindrical electrode contact, the electrode structural parameters can include the height and/or diameter of each cylindrical electrode contact. For an electrode having one or more contacts that are spaced apart from each other along the electrode shaft, the structural parameters can also include an axial spacing between electrode pairs. It will be understood and appreciated that the electrode contacts can have other shapes than a circular cylindrical shape. For example, an electrode contacts can have a substantially C-shaped cross-section, such that the electrode structural parameters can include the radius of curvature, the arc length, and/or an axial length of the contact. Thus, the arc length thus can range from zero degrees (corresponding to no contact) up to 360 degrees (corresponding to a cylindrical type of contact). The electrode structural parameters can include other geometric features (e.g., shape, contours, discontinuities, and the like) and interrelationships for the contacts that form the electrode.

The system 10 can also include a display 32 that can be utilized to represent the results and calculations performed by the design algorithm. For instance, the display 32 can demonstrate a graphical representation, textual representation or a combination graphical and textual information associated with determining an electrode design. As one example, a graphical interface can provide data to the display 32 for overlaying an expected VTA for one or more given designs over the target VTA. Such a representation provides a visual demonstration of expected performance that can help determine which design parameters should be utilized to construct an electrode for given situation.

The system 10 can also include one or more other input or output devices 34. Such devices 34 can provide an interface through which a user can input data as well as control the methods 20 and 28. For example, a user can employ the I/O device 34 to input data, such as instructions to initiate or modify the electrode design procedure. Alternatively, the I/O device 34 can be employed to acquire the VTA data 22, such as from another location in the memory 18, from another storage location, or to acquire the VTA data from another process running on the computer 12 or on another machine. A user can also employ the I/O device 34 to set the range of parameters 30 or to input the patient data 22, the granularity of such parameters as well as to program other parameters being used in the procedure. The I/O device 34 can also be utilized to interface and enable acquisition of data (e.g., imaging data) from an associated imaging device, such as a magnetic resonance imaging (MRI) system, a computer tomography (CT) system or other imaging modality.

Additionally, the system 10 can be utilized to program an implantable pulse generator (IPG) or other stimulation device 36 (e.g., via an interface that communicatively couples the system with stimulation device) based on the design parameters 30 determined to achieve a desired therapeutic effect for a given patient. For instance, the stimulation parameters being programmed to the stimulation device 36 can vary depending on the electrode configuration that has been selected for a given patient. Those skilled in the art will appreciate various types of wired and wireless connections (e.g., wired or wireless) and communication protocols that can be utilized to program the IPG according to the design parameters 30.

Figure 2:
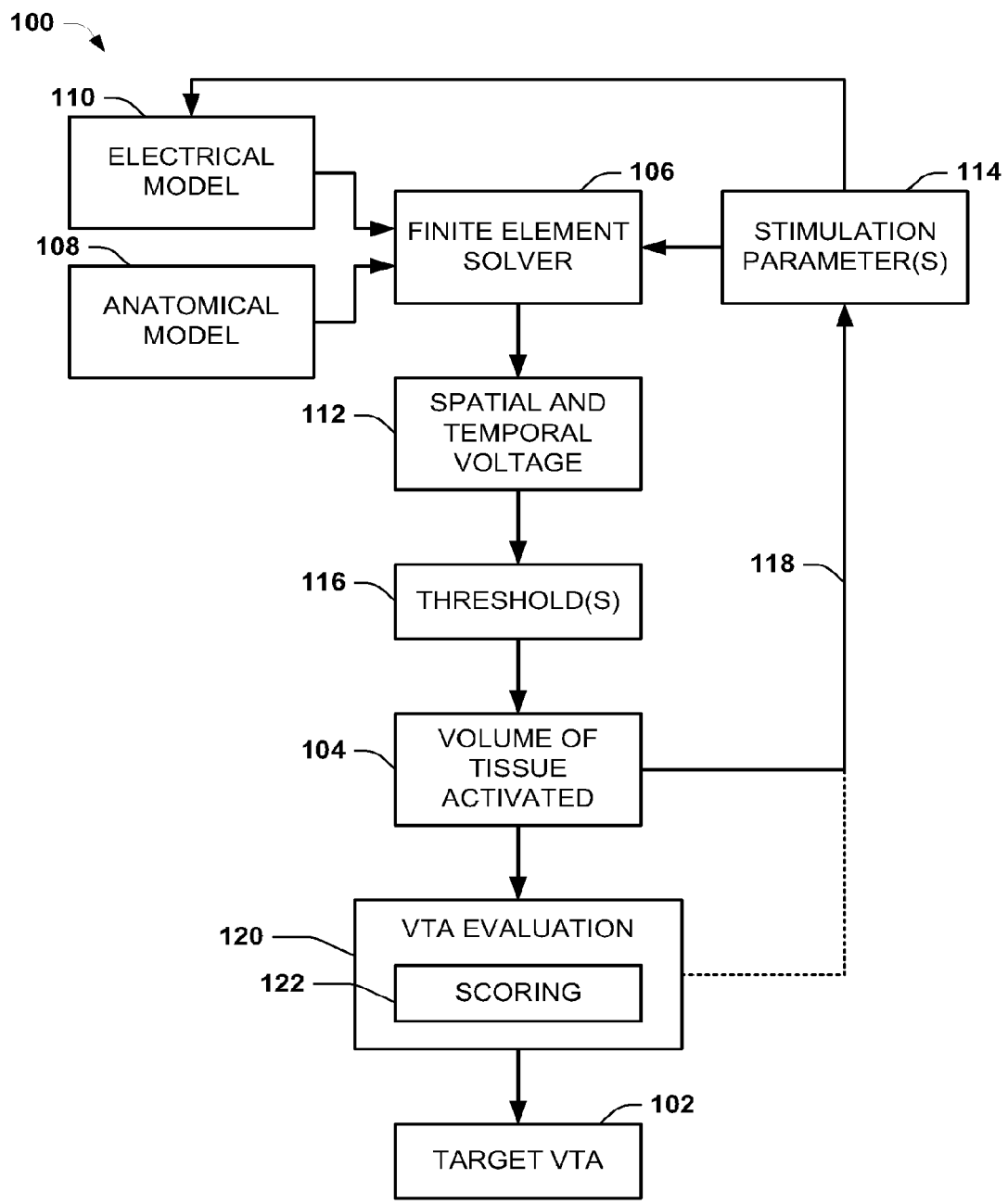
FIG. 2 depicts a functional block diagram of an example approach that can be employed to determine a volume of tissue activation according to an aspect of the invention.

FIG. 2 depicts an example of a block diagram of a system 100 that can be employed to determine a target VTA 102 to achieve a desired therapeutic effect. For instance the target VTA 102 defines an anatomic region for stimulation that is expected to achieve a desired therapeutic effect, such as by generating (and/or inhibiting) propagating action potentials in response to electrical stimulation by one or more electrode contacts located within or near the target VTA. The target VTA can also involve chemical stimulation. As described herein, the target VTA 102 can be utilized to compute one or more electrode geometry parameters (e.g., height, diameter, contact spacing, shape) and stimulation parameters (voltage or current, frequency, pulse width, and waveform shape) for an electrode design to achieve a desired therapeutic effect for a given patient. As part of the design process, the system 100 can also compute a VTA 104 according to corresponding design and stimulation parameters to achieve the target VTA 102. The system 100 can be implemented on a computer or workstation programmed to perform the methods and functions represented in and described with respect to FIG. 2.

The system 100 includes a finite element model (FEM) solver 106 that is programmed and/or configured to determine a spatial and temporal voltage solution 112 based on anatomical and electrical models 108 and 110, respectively. The spatial and temporal voltage solution 112 can also vary according to stimulation parameters 114. For example, the FEM solver 106 can determine a spatial and temporal voltage solution 112 for each (or a subset) of the available stimulation parameters 114 based on the models 108 and 110.

The anatomical model 108 defines the location of the electrode as well as structural features of the anatomical region being modeled for use in the system 100. The anatomical model 108 can be generated using a suitable imaging modality (e.g., MRI or CT imaging), which can be utilized to define the electrode location in the anatomical region and the surrounding anatomical structures. For instance, the preliminary initial contact location can be at the anatomic center of the nucleus. The anatomical model 108 is coupled to the electrical model 110 that characterizes the electric field generated in the anatomical region. The electrical model 110, for example, can characterize tissue conductivity in the anatomical region of interest. As one example, the electrical model 110 can represent the tissue conductivity of the region as being isotropic and homogeneous. As another example, the electrical model 110 can characterize the tissue conductivity as being anisotropic and inhomogeneous. The particular characterization can vary according to the desired accuracy and the particular type of tissue being represented by the anatomical and electrical models. The electrical model 110 can also characterize the electrical properties of the tissue electrode interface as well as the electrode impedance and the electrode capacitance. The electrical model 110 further can reflect the time dependence characteristics at the electrode tissue interface (e.g., via Fourier FEM), such as due to the electrode capacitance.

By way of example, many electrodes (e.g., as used for DBS) are three-dimensional structures and the tissue conductivity of the central nervous system is both inhomogeneous (dependent on location) and anisotropic (dependent on direction). The tissue inhomogeneity and anisotropy surrounding the electrode can alter the shape of the electric field and the subsequent neural response to stimulation. The anisotropy and inhomogeneity of such tissue medium can be accounted for by the FEM solver 106 and the electrical model 110 incorporating 3D conductivities of the tissue. As one example, diffusion tensor imaging (DTI) can be employed to estimate an electrical conductivity tensor of the tissue medium surrounding one or more electrodes.

For instance, diffusion tensor imaging (DTI) can be employed to characterize the diffusional behavior of water in tissue on a voxel-by-voxel basis in terms of a matrix quantity from which the diffusion coefficient can be obtained corresponding to any direction in space. The electrical conductivity tensor ($\sigma$) of a tissue medium is obtainable from the corresponding diffusion tensor (D) determined for the tissue medium. The hypothesized relationship between electrical conductivity and water diffusion in tissue is prompted by the observation that in a structured medium the two processes are related through mutual respect for the boundary conditions imposed by the tissue geometry. It has been determined that a value of the electrical conductivity tensor a can be obtained for each voxel (e.g., from DTI data) using a linear transform of the matrix D:

$$\sigma = (\sigma_e/d_e)D \qquad \text{Equation 1}$$

where $\sigma_e$ is the effective extracellular conductivity, and $d_e$ is the effective extracellular diffusivity.

The diffusion tensors obtained from a corresponding DTI modality can be transformed to conductivity tensors, as discussed above, and incorporated into the electrical model 110 and the FEM solver 106.

The FEM solver 106 thus can solve for the spatial and temporal voltage distribution (e.g., a potential distribution ($V_e$)) 112 that is generated in the tissue medium in response to electrical stimulation in the tissue according to the stimulation parameters 114. The unit of potential distribution can correspond to a single voxel, which can represent a pixel or a set of plural. For example, the FEM solver 106 can determine the potential distribution 112 in the anatomical region of tissue, which can vary according to the tissue model utilized by the FEM solver 106. The potential distribution 112 thus can represent the electric field for each voxel for predefined electrode contact geometry and stimulation parameters. As one example, the FEM solver 106 can be implemented as a Fourier FEM solver that accounts for the capacitance of the electrode-tissue interface under voltage-controlled stimulation. The FEM solver thus can incorporate the DTI-based tissue conductivities and the reactive components of the electrode-tissue interface into a single system of equations.

One or more thresholds 116 can be applied to the potential distribution 112 to ascertain (or predict) whether an activation potential has been achieved for each given unit (e.g., voxel) of the potential distribution. The thresholds 116 can be predefined and applied to the potential distribution 112 to determine a corresponding VTA 104 according to whether a corresponding activating potential has been achieved for each voxel. The VTA 104 can be computed for a defined set of stimulation parameters 114, such that a plurality of VTAs 104 can be determined to define a corresponding search space. The system 100 can re-compute the VTA 104 (and appropriate intermediate values) for each set of stimulation parameters, which procedure is schematically represented by connection 118. That is, a corresponding search space of VTAs 104 can be determined over a range of stimulation parameters 114. The resulting search space of VTAs 104 can be analyzed by an optimization method 120 to ascertain the set of design and stimulation parameters to achieve the target VTA 102.

The thresholds 116 can be implemented by employing a neurostimulation predictor that ascertains whether a corresponding activating potential has been reached for. As one example, a Fourier FEM DBS or spinal cord electrode model can be coupled to an axon or neuron model (e.g., a field-neuron model) for the anatomical region to determine whether an activation potential exists for each voxel. Appropriate thresholds 116 can be defined for the axon or neuron model sufficient to trigger an activating potential in the aggregate FEM analysis.

An alternative approach to the field-neuron simulations described above is the use of an activating function-based technique. One example of such an activating function that can be employed to approximate the neuron response to electrical stimulation is a second difference of the extracellular potential distribution along a neural process ($\partial^2 Ve/\partial x^2$), where Ve represents the potential of a given voxel. The second difference provides a quantitative estimate of the polarization of the axon or neuron in response to an applied electric field. The second difference thus can be applied to the potential distribution to define 3D surfaces that encompass the volume, where $\partial^2 Ve/\partial x^2$ is a suprathreshold for axonal activation for the given stimulation parameters 114.

Figure 3:
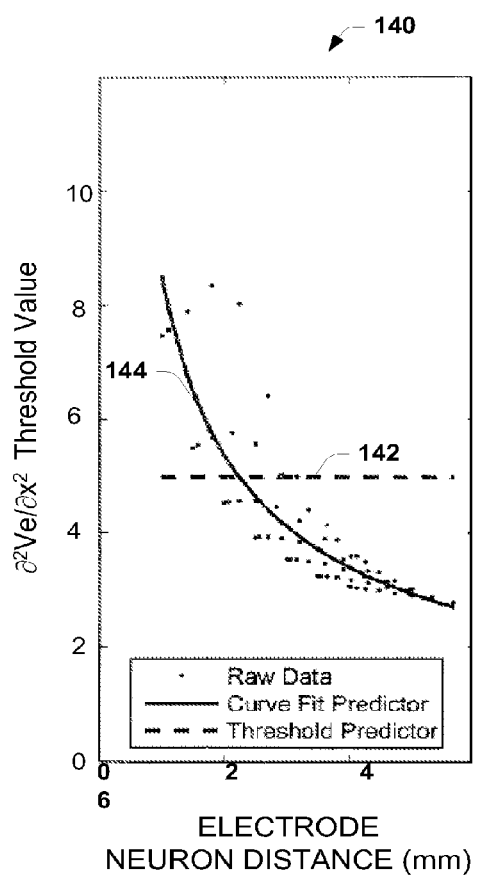
FIG. 3 depicts a graph plotting thresholds that can be applied to predict neural stimulation.

By way of illustration, FIG. 3 depicts a graph that includes an example of $\partial^2 Ve/\partial x^2$ function that can be utilized as a predictor of neural activation. In the example of FIG. 3, the $\partial^2 Ve/\partial x^2$ values are plotted as a function of electrode-axon distance measured from the center of the electrode. An absolute threshold (indicated by a dashed line 142) is one type of simple predictor that can provide a low level of accuracy in predicting neural activation. An alternative approach is to perform a curve fitting function to provide a corresponding variable threshold (indicated by solid line 144) that approximates clinical raw data.

Yet another alternative approach is to determine the $\partial^2 Ve/\partial x^2$ threshold values as a function of pulse width and voltage. Specifically, $\partial^2 Ve/\partial x^2$ threshold values are recorded, and these values are expressed as a function of cathodic voltage (V) times pulse width (PW, µs). This expression allows two stimulation parameters to be condensed into a single number for prediction of thresholds. Further, threshold values recorded this way were found to be valid for a wide range of electrode designs and stimulation parameters. These values can then be used to create 2D spatial contours that are swept around the z-axis to define the VTA volume. For purposes of volume calculations, it is often convenient to describe the VTA contours with analytical functions. For example, each contour can be described by an ellipse:

$$(x-x0)^2/a2+(y-y0)^2/b2=1 \qquad \text{Equation 2}$$

where x0, y0 is the center of the ellipse, and
a and b are the semimajor and semiminor axes, respectively (assuming b<a).

The semimajor and semiminor coefficients are calculated from the following: a=distance of threshold value from electrode contact along x-axis; b=maximum y value of 2D threshold contour. In this example contour, the center of the electrode contact can be defined as being located on the origin and the center of each ellipse is x0=a, y0=0. With this method, $\partial^2 Ve/\partial x^2$ threshold values and VTA volumes can be predicted for a wide range of electrode designs and stimulation parameters.

Figure 4:
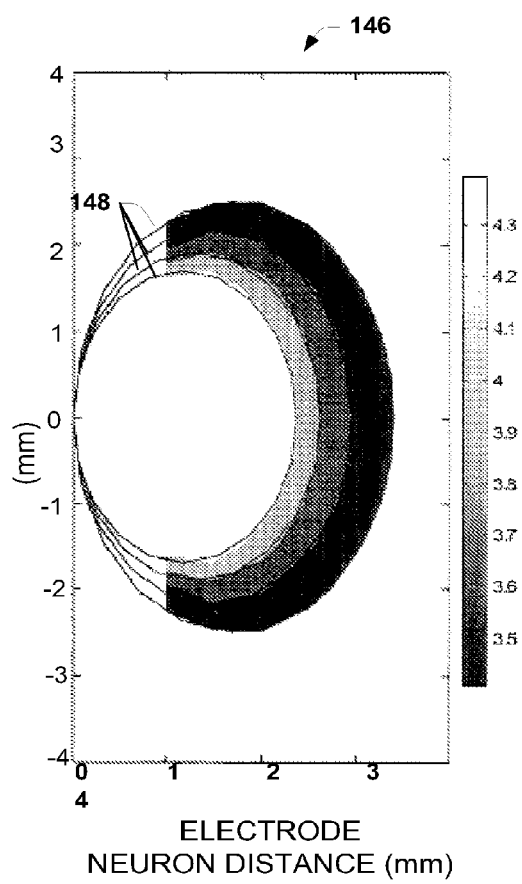
FIG. 4 depicts a plot of a second difference-based approach that can be used to predict neural stimulation.

FIG. 4 depicts an example of spatial ellipsoid-based predictors 148 that can be implemented as described above. The predictors 148 can be applied to a variety of electrode design and stimulation parameters. In the example of FIG. 4, corresponding $\partial^2 Ve/\partial x^2$ predictors for voltage-controlled stimulation are overlaid on filled $\partial^2 Ve/\partial x^2$ threshold contours, as represented by the associated indicator bar located to the right of the figure. The $\partial^2 Ve/\partial x^2$ threshold contours can be generated from the integrated field neuron model, as described herein.

Figure 5:
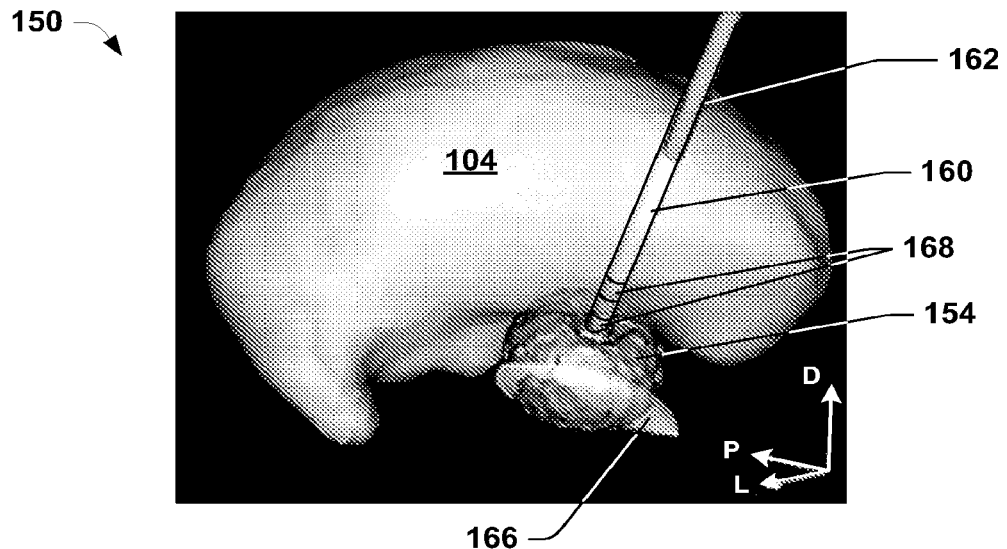
FIG. 5 depicts an example of a volume of tissue activation that can be ascertained for an isotropic tissue medium.
Figure 6:
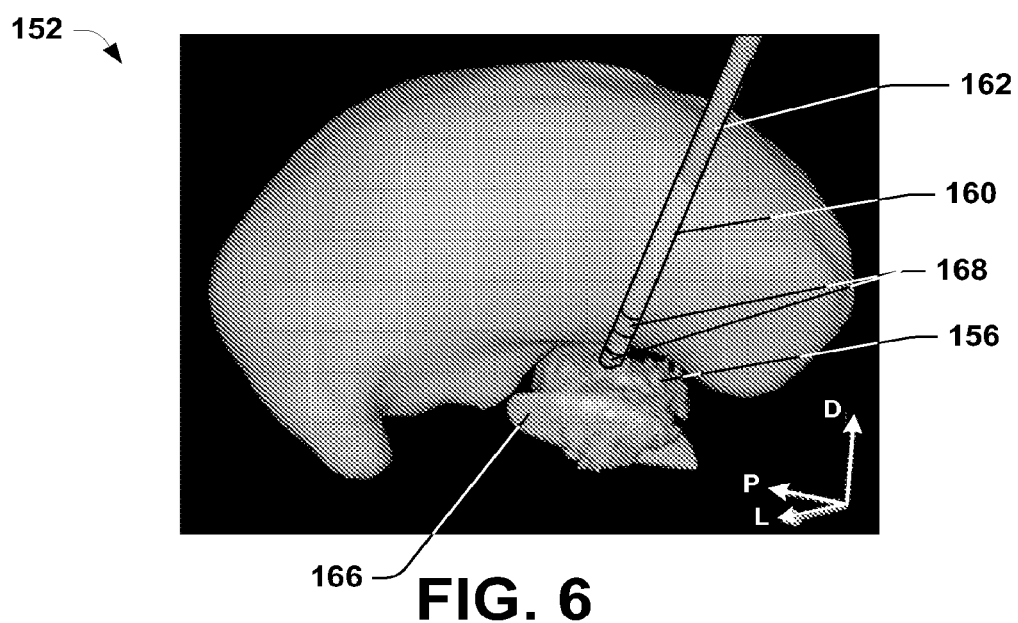
FIG. 6 depicts an example of a volume of tissue activation that can be ascertained for an anisotropic and inhomogeneous tissue medium.

By way of further example, FIGS. 5 and 6 depict example images 150 and 152, respectively, demonstrating different VTAs that can be determined for deep brain stimulation by applying different tissue models for the same activating function. For sake of consistency, similar reference characters refer to the same structural and anatomical parts in each of the FIGS. 5 and 6.

In FIG. 5, the VTA, indicated at 154, is determined for a tissue model where the tissue medium is represented as being isotropic and homogeneous. In FIG. 6, the image 152 demonstrates the VTA, indicated at 156 for a model that represents the tissue medium as being inhomogeneous and anisotropic (a more complex and usually more accurate tissue representation), such as a DTI-based tissue medium. A comparison of the approaches demonstrates the resulting differential activation of surrounding anatomical structures.

Figure 8:
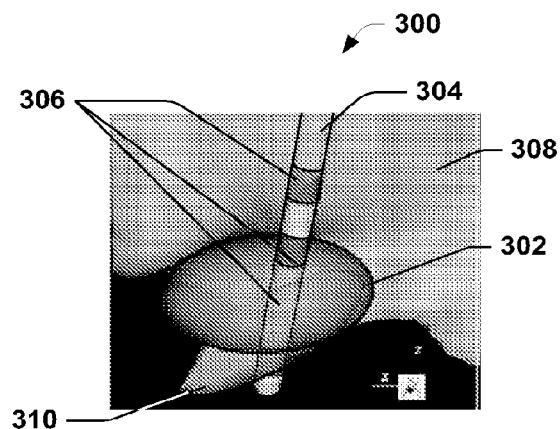
FIG. 8 depicts an example image of a target VTA that can be used for designing an electrode according to an aspect of the invention.

Each of the tissue models utilized to derive the images of FIGS. 5 and 6 includes a tissue encapsulation layer 160 around the electrode shaft 162. The electrode shaft 162 extends through the thalamus 164 and terminates with its distal end located within or adjacent the subthalamic nucleus (STN) 166. A plurality of electrode contacts 168 are disposed in a spaced apart relationship along the length of the shaft 162. The VTA 154 corresponds to a volume of tissue within a boundary defined by activating function applied for a given set of stimulation parameters one of the contacts 168 within the STN 166. In FIG. 8, the VTA 156 similarly corresponds to a volume of tissue within a boundary defined by activating function applied for the same given set of stimulation parameters at a single contact within the STN 166. The VTA 154 (FIG. 5) and the VTA 156 (FIG. 6) generated under the two conditions were matched for electrode impedance.

Figure 21:
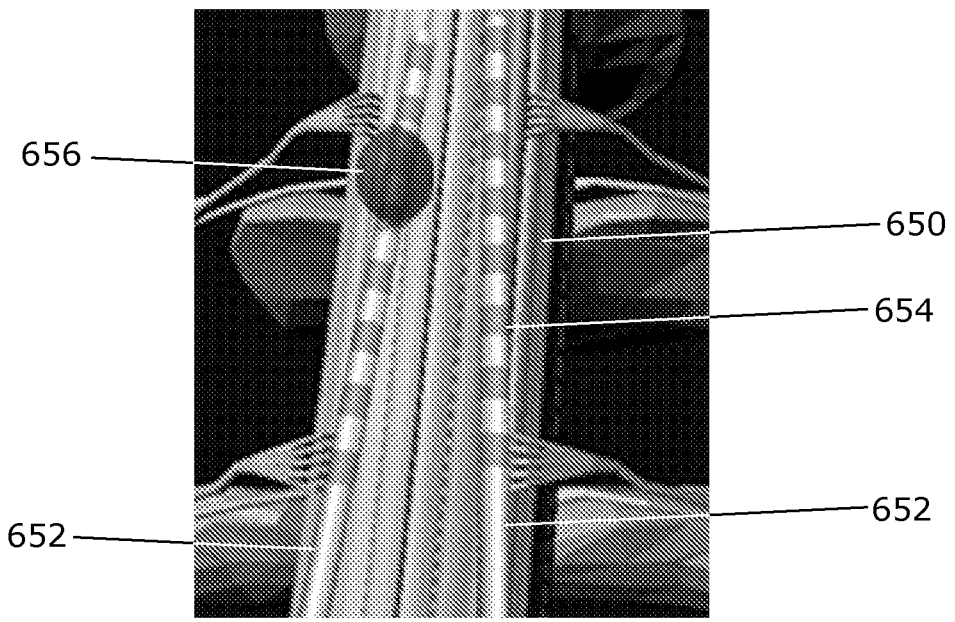
FIG. 21 depicts an example of a volume of tissue activation produced by an electrode implanted adjacent a spinal cord, which is being represented as an isotropic tissue medium.
Figure 22:
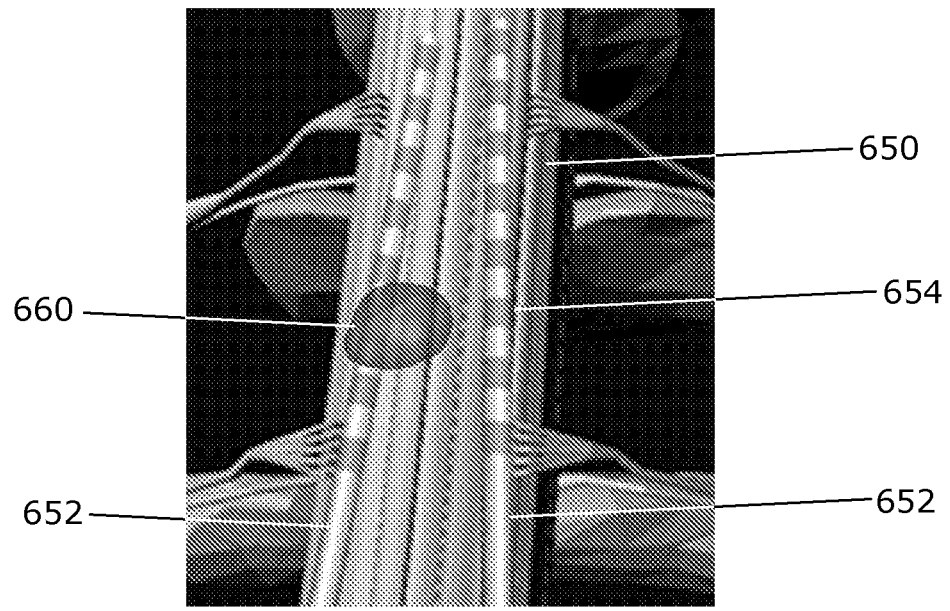
FIG. 22 depicts an example of a volume of tissue activation produced by an electrode implanted adjacent a spinal cord, which is being represented as an anisotropic and inhomogeneous tissue medium.

FIGS. 21 and 22 show examples of how VTAs for spinal cord stimulation can be displayed by the present invention. These figures demonstrate different VTAs that can be determined for spinal cord stimulation by applying different tissue models for the same activating function. FIG. 21 shows an image of the spinal cord 650 and two electrodes 652 positioned adjacent the spinal cord 650, which is represented as being isotropic and homogeneous in the tissue model. Each of electrodes 652 has multiple electrode contacts 654. The volume of tissue activation 656 produced by the left-sided electrode for a given set of stimulation parameters is shown. FIG. 22 shows an image of the spinal cord 650 and two electrodes 652 positioned adjacent the spinal cord 650, which is represented as being anisotropic and inhomogeneous in the tissue model. The volume of tissue activation 660 produced by the left-sided electrode for a given set of stimulation parameters is shown. A comparison of FIGS. 21 and 22 demonstrates how the different tissue models result in different volumes of activation.

Referring back to FIG. 2, the system 100 also includes a VTA evaluation block 120 that is operative to search through the VTAs 104 to determine which VTA best matches the target VTA 102 for achieving a desired therapeutic effect. The evaluation block 120 can be implemented as a computer-implemented (or computer-assisted) algorithm that evaluates the candidate VTAs 104 in the search space. Each of the candidate VTAs 104 thus has a set of electrode design and stimulation parameters that provides the candidate VTA. The evaluation block, for example, can include a scoring function 122 that assigns a score to each candidate VTA 104. The score can help a user select the set of design and stimulation parameters to best achieve the target VTA 102 from the VTA search space. Alternatively, the evaluation block 120 can automatically select the VTA matching the target VTA 102 based, at least in part, on the score provided for each VTA 104 in the search space. The VTAs 104 and their scores can be displayed to a user, such as by providing corresponding data to a display or other output device (e.g., a printer).

As one example, the evaluation algorithm of the evaluation block 120 can employ one or more criteria that establishes: (a) one or more regions in which activation is desired; or (b) one or more regions in which activation should be avoided. The criteria can be provided as part of a statistical atlas brain or other neural tissue such as the spinal cord from which the target VTA was ascertained for a given patient. For example, the scoring function 122 can determine a score of how each candidate VTA maps against desired and undesired regions relative to the target VTA 102. In one example, the scoring function 122 computes the score as a function of the number of VTA voxels that map to the one or more regions in which activation is desired, and the number of VTA voxels map to the one or more regions in which activation is undesired. As another example, these two quantities may be weighted differently such as, for instance, if avoiding activation of certain regions is more important than obtaining activation of other regions (or vice-versa). In yet another example, these two quantities may be used as separate scores. As another example, the evaluation block 120 and scoring function 122 can be implemented based on documented therapeutic effect and assign a corresponding raw score to each VTA and its associated stimulation parameters.

By way of further example, to determine a target VTA for treatment of Parkinson's disease, the raw score provided by the scoring function 122 can correspond to documented improvement according to blinded UPDRS evaluation. The VTAs can also be designated with one or more primary symptoms of improvement, such as rigidity, bradykinesia, and/or tremor. The VTA can also be designated as being non-therapeutic when a given VTA is identified with a clinically defined side effect type (e.g., muscle contraction, parasthesia, and the like). The designation symptomatic relief and side effects can also be weighted and applied to scoring criteria according to the perceived conditions (e.g., through clinical testing) associated with a given VTA. Other scoring criteria can exist for Parkinson's disease as well as for other types of disorders that can be utilized by the evaluation block 120. The scoring function 122 thus can provide an indication of the therapeutic and non-therapeutic effect associated with the VTAs 104, which can be weighted accordingly. Such scoring can be ascertained by evaluating the candidate VTAs 104 relative to a statistical VTA data structure, such as is utilized to determine the target VTA for the given patient.

As a further example, VTA data structure can be provided in the form of a 3D probabilistic map or functional VTA atlas. VTA data, for example, can be acquired for a plurality (e.g., hundreds or thousands) of patients so that VTA 104 for each patient can provide quantitative relationship between the VTA and a desired therapeutic effect for the patients. For example, each of the VTAs 104 can be broken up into a voxelized grid in which each voxel retains the score determined for the respective VTA. The voxel matrix can be statistically analyzed to provide a corresponding probability value for each voxel in the matrix that represents a statistical score for each voxel in the functional atlas. With a sufficiently large search space, a corresponding target VTA thus can be identified based on the aggregate set of VTAs 104 in the search space. Side effect pathways can also be integrated into the 3D probabilistic map of therapeutic VTAs as areas to avoid when defining the target VTA 102 for a given patient. The resulting probabilistic VTA map can be utilized to determine the target VTA based on imaging data for a given patient and a clinical assessment of the given patient. The assessment can involve qualitative and/or quantitative assessment of the patient's condition, such as described herein.

Figure 7:
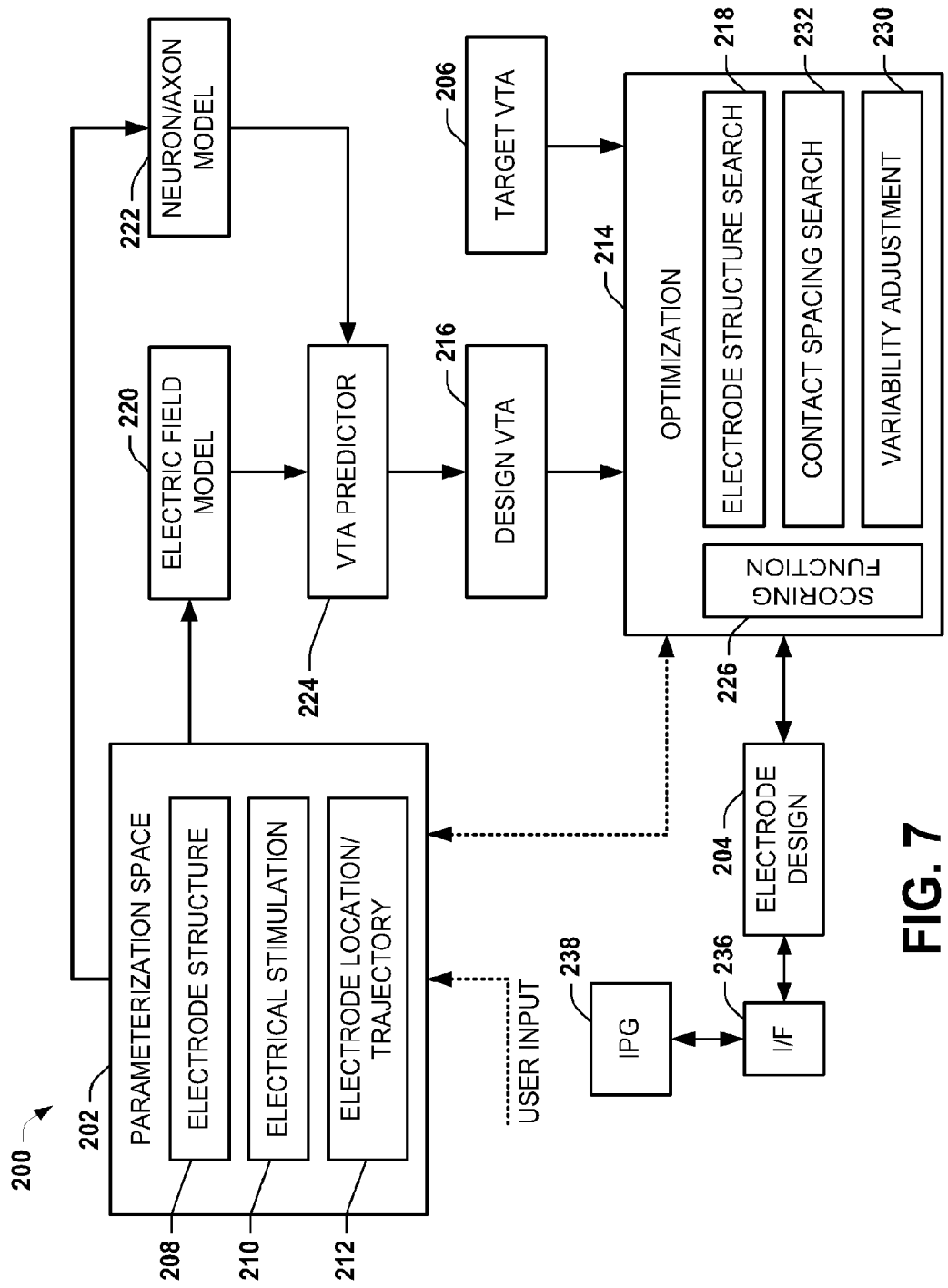
FIG. 7 depicts an example of a design system that can be implemented according to an aspect of the invention.

FIG. 7 depicts an example of an electrode design system 200 that can be implemented according to an aspect of the invention. The system 200 can be implemented as computer-executable instructions running in one or more computers or other processor-based systems. The system 200 includes a parameterization space 202 that includes parameters that represent one or more design parameters that can be varied to provide an electrode design 204, electrical stimulation and/or chemical stimulation for achieving a desired therapeutic effect. The purpose of the system 200 is to determine which parameter or combination of plural design parameters can provide a VTA that best matches a target VTA 206 for a given patient. One or more of the parameters for the electrode design or available ranges can be established by a user input, for example.

The target VTA 206 defines a region of tissue that, if stimulated by an electric field from the electrode located therein, generates an action potential that has been determined to achieve a desired therapeutic effect. The therapeutic effect and the location of the target VTA 206 can vary according to the disorder of a particular patient. The target VTA 206 can be predetermined for a given patient, such as described herein.

As an example, FIG. 8 depicts an image 300 that includes a representation of a target VTA 302 that can be utilized to determine the electrode design parameters for a given target nucleus. As shown in FIG. 8, an electrode 304 includes a plurality of contacts 306, at least one of which is located in the target VTA 302. The electrode shaft extends through the thalamus 308 and through at least a portion of the STN 310. In the example of FIG. 8, the target VTA 302 comprises a region that encompasses the dorsal STN and ZI/H2, such as represents a preliminary definition of a target VTA for STN DBS. Those skilled in the art will appreciate that the design system 200 (FIG. 7) is applicable to determining target VTAs for other nuclei in the brain as well as in other anatomical regions such as other neural tissue including the spinal cord and peripheral nerves.

Referring back to FIG. 7, the parameterization space 202 includes a range of electrode structure parameters 208. For the example of an electrode having a plurality of cylindrical electrode contacts, the electrode structure parameters 208 can include the height, diameter and spacing (or distribution) of the electrode contacts along the electrode shaft. As an example, a predefined range of values for the height and diameter parameters can be stored as part of the parameterization space (e.g., by setting limits for minimum and maximum height and diameters). Relationships between parameters can also be parameterized, such as the aspect ratio (d/h), in the parameterization space 202. The aspect ratio further can be utilized to constrain the optimization procedure, such as by limiting the search space to a predefined range of aspect ratios (e.g., d/h<some predefined value), which can be set according to the shape and size of the target VTA 206.

The parameterization space 202 can also include electrode stimulation parameters 210, such as voltage or current amplitude, frequency, pulse width and pulse shape. The stimulation parameters can be applied to one or more electrode contacts uniformly or different set stimulation parameters can be applied to each electrode contact independently of the other electrode contacts. The contact location and trajectory of the electrode within an anatomical region can be included as parameters 212 in the parameterization space 202 identifying relative electrode and contact placement in an anatomical region. For example, the contact location can be centered in the anatomical region defined by the target VTA 206 and the trajectory can be set to a corresponding standard trajectory for the target nucleus. Alternatively, such parameters can be varied, as described with respect to other example embodiments described herein.

An optimization method 214 controls the parameter searching over the parameterization space 202. The optimization method 214 can evaluate a design VTA 216 for an instance of the parameterization space 202 relative to the target VTA 206 to ascertain which instance (or subset of instances) of the parameterization space provides a design VTA that best matches the target VTA. The optimization method 214 can include one or more search algorithms programmed to determine the electrode design 204.

As one example, the optimization method 214 can include an electrode structure search 218 that is programmed to search the parameterization space 202 to determine one or more instances of electrode structure parameters. For example, the electrode structure search 218 can initialize the parameterization space 202 to set the electrode structure parameters 208 (height and diameter) to predetermined dimensions, such as can be arbitrarily set or can be set based on various criteria (e.g., empirical or clinical studies). The electrode location/trajectory parameters 212 can remain fixed during application of the electrode structure search 218. The electrical stimulation parameters 210 can be varied for a given set of electrode structure parameters 208 to provide maximal design VTA coverage relative to the target VTA 206, as described herein.

The system 200 includes an electrode field model 220 and a tissue model 222 that are employed by a VTA predictor 224 to determine the design VTA 216 for a given instance or over a set of plural instances of the parameterization space 202. The VTA predictor 224 predicts the neural response to stimulation, corresponding to the design VTA 216, by applying the potential distribution of the electrical field model 220 to the neuron/axon model 222. The neural response to extracellular stimulation is dependent on several factors, including, for example: (1) the electrode geometry (e.g., the electrode structure parameters 208); (2) the electrode stimulation parameters 210 (e.g., stimulus waveform, stimulation frequency, pulse width, etc.); (3) the shape of the electric field (e.g., as determined by the inhomogeneous and anisotropic bulk tissue properties); (4) the neuron geometry; (5) the neuron position relative to the stimulating electrode; and (6) the neuron membrane dynamics. Some or all these factors can be represented in the electric field model 220 and the neuron/axon model 222.

As one example, the electric field model 220 can be implemented as a computer-solvable FEM mesh based on the electrode structure parameters 208 and the stimulation parameters 210 in the parameterization space 202. The electric field model 220 thus can include a stimulating electrode model that represents the morphology (or structure) of the electrode, as established by the electrode structure parameters 208 employed by the electrode structure search 218. The electric field model 220 can also include a representation of the conductivity of a thin layer of tissue encapsulating the particular electrode, which provides the electrode tissue interface. The electric field model 220 can also explicitly represent the electrode impedance and the electrode capacitance. The electric field model 220 also includes tissue conductivity model that represents the anatomical structure surrounding the electrode. As described herein, the tissue conductivity model can include data that represents inhomogeneous or anisotropic properties of the tissue near the stimulation electrode, such as can be obtained by DTI imaging or by using other techniques described herein. Alternatively, the tissue conductivity model might include data that represents tissue near the stimulation electrode as being homogeneous and isotropic, such as described herein. The electric field model 220 thus represents a potential distribution in the tissue medium for a given set of parameters (e.g., electrode structure and electrode stimulation parameters) in parameterization space 202.

The neuron/axon model 222 can include a multi-compartment neuron or axon model that positions the modeled neurons or axons at specifiable positions along one or more nerve pathways in the FEM mesh defined by the electric field model 220. In addition to properties of individual neurons, the neuron/axon model 222 may depend on one or more of the parameters (e.g., electrode structure parameters 208 and electrical stimulation parameters 210) of the stimulation being modeled. For example, the stimulation pulse width will affect the neuron response. Therefore, in one example, the neuron/axon model 222 can be tailored to a specific value for one or more DBS stimulation parameters or stimulation parameters for other neural tissue such as the spinal cord or a peripheral nerve. By way of further example, the nerve pathways can be ascertained using DTI-derived imaging data, or by using anatomic atlas data, or any other appropriate technique.

Those skilled in the art will understand appreciate various neuron models or axon modeling techniques that could be employed in the system 200. An example of an axon model is described in Cameron C. McIntyre et al., "Modeling the Excitability of Mammalian Nerve Fibers: Influence of Afterpotentials on the Recovery Cycle," J. Neurophysiology, Vol. 87, February 2002, pp. 995-1006, which is incorporated by reference herein in its entirety, including its disclosure of axon models. In another example, a more generalized neuronal model can be used, an example of which is described in Cameron C. McIntyre et al., "Cellular Effects of Deep Brain Stimulation Model-Based Analysis of Activation and Inhibition," J. Neurophysiology, Vol. 91, April 2004, pp. 1457-

1469, which is incorporated by reference herein in its entirety. The neuron/axon model 222 describes how the neurons will respond to an applied electric field; namely whether the neuron will fire and whether the neurons will generate a propagating action potential.

As a further example, the neuron model 222 geometries are typically broken up into many (e.g., hundreds) of compartments. The VTA predictor 224 can co-register the various compartments of the neuron/axon model 222 within the FEM mesh of the electric field model 220. This co-registration allows calculation of the extracellular potentials from the applied electric field along the complex neural geometry. After the extracellular potentials are determined for each neural compartment as a function of time during the applied stimulation, for each neural position relative to the electrode, the neuron/axon model 222 can be used to test whether the applied stimulus exceeded the neural threshold that triggers an action potential.

As another example, using the neuron/axon model 222 to simulate how the neurons (e.g., which are located as determined from the DTI-derived conductivity data) behave, the threshold value of the second difference of electric field that will result in such propagating action potentials can be calculated. The stimulating influence of the electric field (as represented by the electric field model 220) is applied to the neuron/axon model neurons to define a threshold value. This threshold value can then used to define the boundary of the design VTA in the non-uniform conductivity tissue, similar to as discussed above with respect to FIG. 2.

The electrode structure search 218 can vary the electrode height and diameter over the range of predefined values, such as mentioned above. Corresponding design VTAs can be determined over the range of parameter values. Those skilled in the art will appreciate that various constraints that can be programmed into the electrode structure search 218 or into the parameterization space 202 to reduce computational complexity of the design system. For example, it may be desirable to constrain the diameter to height (aspect) ratio to remain below a predetermined value (e.g., d/h>1), which value further can vary according to the shape and volume of the target VTA 206. Those skilled in the art will appreciate various ways to quantify the shape and size of the target VTA 206 such that an appropriate VTA aspect ratio can be established to constrain the optimization accordingly.

The optimization method 214 can also include one or more scoring functions 226 that are employed to evaluate at least some of the design VTAs 216 in the search space relative to the target VTA 206. Different search components of the optimization method can utilize the same scoring function or different scoring functions can be utilized for different searches. As one example, each design VTA (corresponding to an iteration of the electrode structure search 218) can be scored according to the following equation:

$$\text{Score} = (\text{VTA}_{in\ target}/\text{VTA}_{target}) * (1 - \text{VTA}_{out\ target}/X\text{volume}), \quad \text{Equation 3}$$

where:
$\text{VTA}_{in\ target}$ corresponds to the portion of the design VTA 216 that resides within the target VTA 206,
$\text{VTA}_{out\ target}$ corresponds to the portion of the design VTA 216 that resides outside of the target VTA 206, and
Xvolume defines the penalty for stimulation spread outside of the target VTA.

The highest scoring electrode design VTA will represent the maximal volume overlap between the stimulation VTA and the target VTA while providing a penalty for VTA spread outside of the target VTA. In practice, variants of the above scoring equation (as well as other scoring functions) can be used to hone in on an appropriate value for the Xvolume parameter.

As part of the electrode structure search 218, one or more of the electrode stimulation parameters 210 can be adjusted for the given electrode structure design so that the design VTA spreads to or near to the edge of the target VTA 206. Alternatively, the electrode structure search 218 can iteratively adjust one or more electrode structure parameters while the electrode stimulation parameters remain constant, generating a new design VTA 216 for each iteration. Those skilled in the art will appreciate various approaches that can be utilized to generate design VTAs 216 over the entire or a subset of the parameterization space. Those skilled in the art will further appreciate approaches that can be employed to constrain the parameterization space to expedite the optimization process.

The results of the electrode structure search 218 can provide one or more electrode designs 204. For example, the electrode structure search 218 can provide a plurality of electrode designs (e.g., having defined electrode structure and electrode stimulation parameters) that result in respective design VTAs that best match the target VTA 206.

Figure 9:
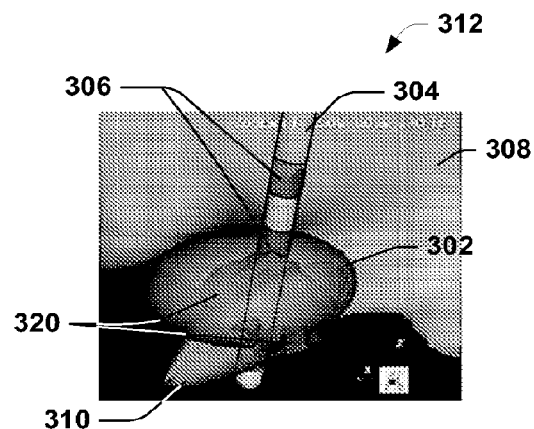
FIG. 9 depicts an example of a first design VTA overlayed on the image of FIG. 10.
Figure 10:
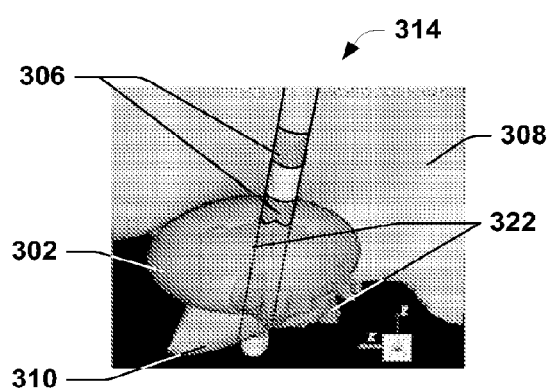
FIG. 10 depicts an example of a second design VTA overlayed on the image of FIG. 10.
Figure 11:
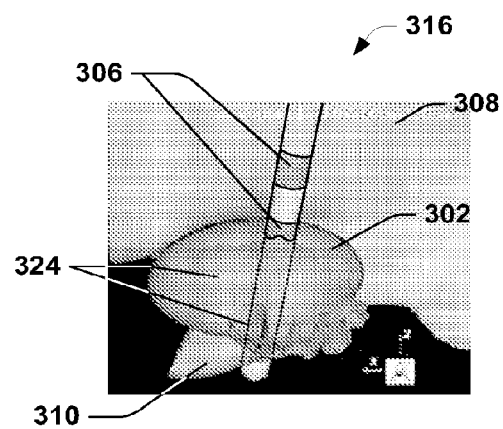
FIG. 11 depicts an example of a third design VTA overlayed on the image of FIG. 10.

By way of illustration, FIGS. 9, 10 and 11 depict images 312, 314 and 316, respectively, that include example design VTAs generated for an electrode contact of a given electrode structure (e.g., as defined by electrode structure parameters 208) 304 for different stimulation parameters. In each of FIGS. 9, 10 and 11, the same reference numbers are used to refer to the same structural parts as introduced with respect to FIG. 8. The VTAs generated at the respective contact result in some amount of $\text{VTA}_{in\ target}$ and some amount of $\text{VTA}_{out\ target}$, both of which vary as a function of the stimulation parameter settings and the electrode contact geometry.

In FIG. 9 the image 312 includes a design VTA 320 constructed for a stimulation voltage of about −2 V at the respective contact. In FIG. 10, the image 314 includes a design VTA 322 for a stimulation voltage of about −2.5 V at the respective contact. In FIG. 11, the image 316 includes a design VTA 324 for a stimulation voltage of about −3 V at the respective contact.

In FIGS. 8, 9, 10 and 11, for purposes of simplicity of explanation and for sake of comparison, it is assumed that the electrode geometry remains constant. By applying the above-described scoring criteria, the example of FIG. 10 has the highest score and, thus, can be utilized to establish the electrical stimulation parameters 210 associated with the given set of electrode structure parameters 208 for the electrode design of FIG. 7. It will be appreciated that more than three different stimulation parameters can (and typically will) be evaluated and scored as part of the electrode structure search 218.

Figure 23:
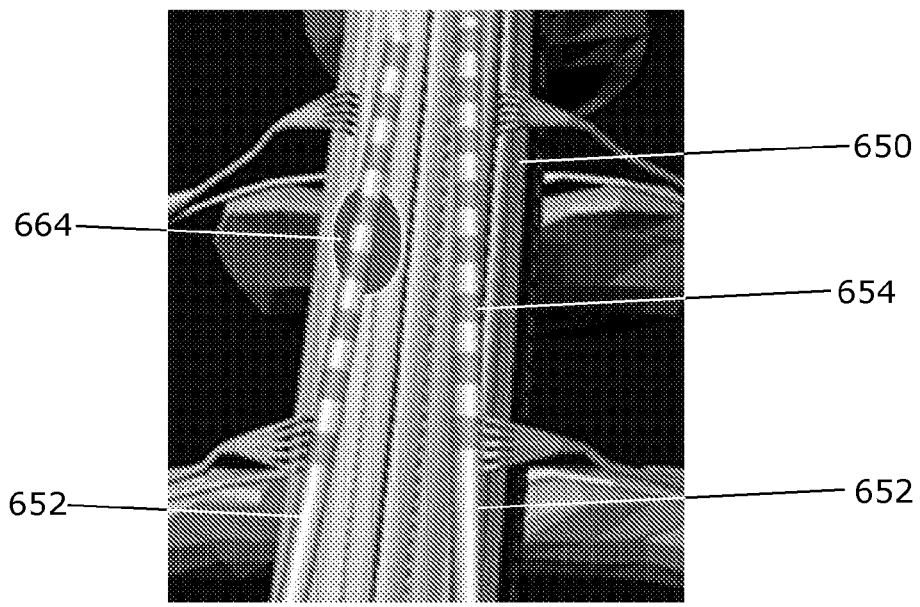
FIG. 23 depicts an example of a target VTA that can be used for designing an electrode for spinal cord stimulation.
Figure 24:
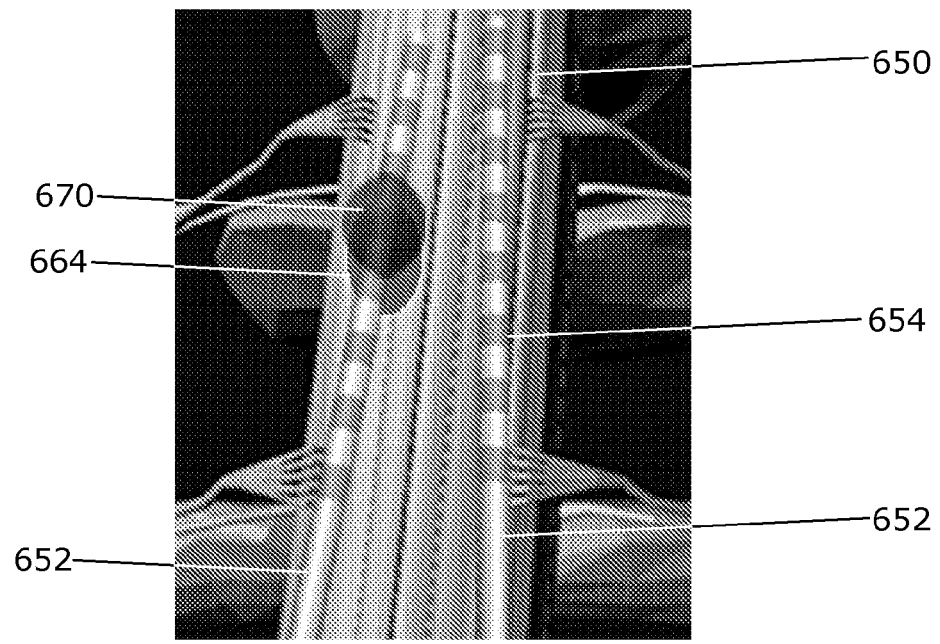
FIG. 24 depicts an example of a first design VTA overlayed on the image of FIG. 23.
Figure 25:
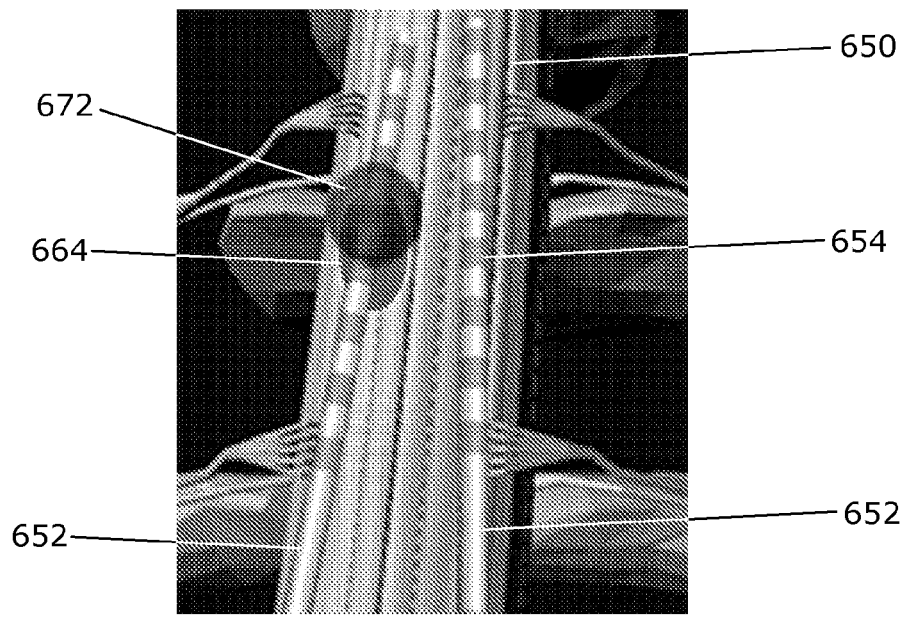
FIG. 25 depicts an example of a second design VTA overlayed on the image of FIG. 23.
Figure 26:
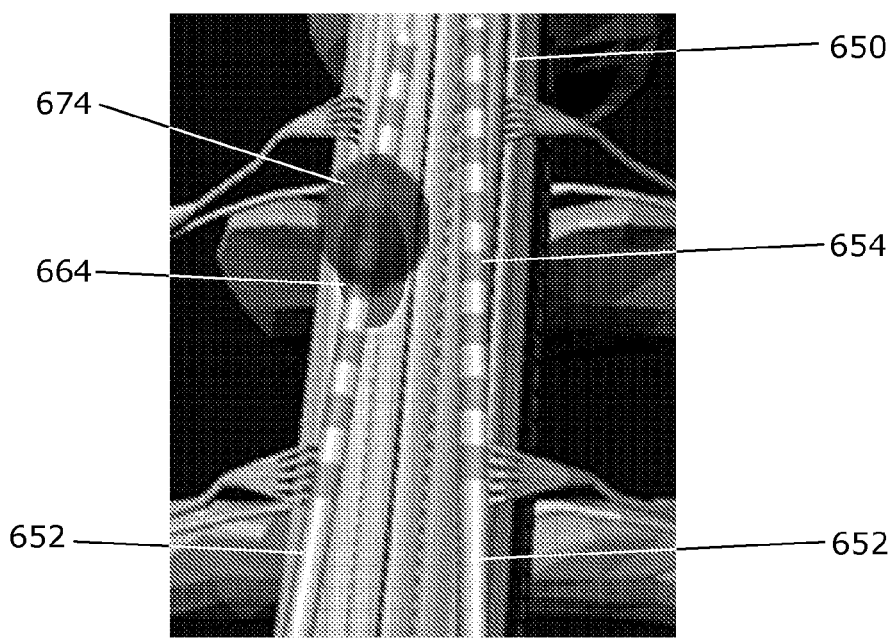
FIG. 26 depicts an example of a third design VTA overlayed on the image of FIG. 23.

The present invention can also be used for designing electrodes for spinal cord stimulation. As an example, FIG. 23 shows an image of a spinal cord 650 and two electrodes 652 positioned adjacent the spinal cord 650. Each of electrodes 652 has multiple electrode contacts 654. A target VTA 664 encompasses a region of the spinal cord that is targeted for stimulation. As such, the design system 200 (FIG. 7) can be used for designing an electrode that targets this region of the spinal cord. The design VTAs are generated for an electrode contact of a given electrode structure for different stimulation parameters. The design VTAs are compared against the target VTA 664. As seen in these figures, the design VTAs have some amount of volume being within target VTA 664 and some amount of volume being outside of target VTA 664, and both will vary according to different stimulation parameter settings and the electrode contact geometries. In each of FIGS. 24, 25, and 26, a design VTA is constructed at different stimulation voltages at the respective contact and compared against target VTA 664. FIG. 24 shows design VTA 670 generated at one stimulation voltage; FIG. 25 shows design VTA 672 generated at another stimulation voltage; and FIG. 26 shows design VTA 674 generated at another stimulation voltage. In FIGS. 23, 24, 25, and 26, for purposes of simplicity of explanation and for sake of comparison, it is assumed that the electrode geometry remains constant. By applying the above-described scoring criteria, the example of FIG. 26 has the highest score. Accordingly, this design VTA can be used to establish the electrical stimulation parameters associated with the given set of electrode structure parameters for the electrode design.

Referring back to FIG. 7, it is again noted that the electrode location/trajectory parameters 212 can remain fixed during the optimization of electrode design associated with the electrode structure search 218 and a contact spacing search 232 (when implemented). The surgical trajectory for electrode implantation in a given nucleus is relatively standardized. As one example, a general trajectory for STN DBS approximately 65 degrees up from the axial plane and approximately 10 degrees off the saggital plane. As another example, the general trajectory for GPi DBS can be approximately 70 degrees up from the axial plane and approximately 5 degrees off the saggital plane. The particular trajectory used in an individual patient, however, is chosen based on pre-operative imaging data to avoid major blood vessels, sulci, and the ventricles.

The electrode/location and trajectory parameters 212 thus can be set to standard electrode trajectories for a given nucleus (adjusted to avoid major blood vessels, sulci, and the ventricles) with the contact location at the anatomical center of the nucleus. The parameter values can remain fixed during the electrode structure search 218, such as described above. After a subset of one or more electrode designs has been determined for the target VTA, the optimization method 214 can vary electrode structure and stimulation parameters to accommodate surgical variability (e.g., associated with surgical placement of the electrode) and anatomical variability (e.g., associated with imaging techniques for determining anatomical and electrical models).

The optimization method 214 can also include a variability adjustment component 230. The adjustment component 230 can refine a portion of the search space to reevaluate the efficacy of one or more electrode designs to account for variability that would be expected clinically. One source of clinical variability is the stereotactic accuracy of the electrode placement. For example, it has been determined that there exists approximately 1 mm of uncertainty in all directions in three dimensional space when implanting many types of electrodes, such as DBS electrodes. Therefore, the variability adjustment component 230 can reevaluate the electrode structure parameters for each of a plurality of best-performing electrode designs 204, such as by adjusting the electrode location/trajectory parameter 212 to reflect the approximately 1 mm of uncertainty in three-dimensional space.

As an example, a plurality (e.g., two or more, such as five) of the top scoring electrode designs 204 for the target VTA 206 can be subjected to further analysis including scoring. For example, the electrode location and trajectory can be incrementally adjusted (e.g., relative to the geometric center of the target VTA) in the dorsal/ventral, anterior/posterior, and medial/lateral directions) and the resulting design VTAs 216 can be scored according the sub-optimal electrode placements. The electrodes location parameters can be adjusted, for example, in predetermined increments that are less than or equal to the amount of defined variation.

The surgical trajectory of the electrode in the 3D anatomical region can also be varied, such as in a plurality of increments over a range (e.g., +/−5 degrees) relative to the axial plane and in similar increments over a range (e.g., +/−5 degrees) relative to the saggital plane. Each of the finalist DBS electrode designs 204 will thus be assigned a plurality of scores for each associated design VTAs 216 resulting from the incremental adjustments (to accommodate variation in location and trajectory). The set of VTA scores for each of the incrementally adjusted respective electrode design 204 being reevaluated can be aggregated to provide an aggregate total score for each design. The average VTA scores for each electrode design 204 further can be averaged and the highest scoring electrode design can be selected as representing an optimal DBS electrode contact for the given target nucleus or other optimal neural tissue electrode contact such as a spinal cord electrode contact or a peripheral nerve electrode contact. The same scoring function 226 (e.g., Equation 3) can be utilized by the variability adjustment component 230 as is used by the electrode structure search 218. Alternatively, different scoring functions could be utilized, such as by applying weighting differently according to variations in the electrode/trajectory parameters 212 differently (e.g., imposing an increased penalty as the variations increase).

By way of example, existing neurostimulation devices are being equipped with current steering capabilities (e.g., implantable pulse generators having 8 or 16 independent current sources). The existence of current steering technology in neurostimulation becomes an attractive mode of operation in a situation where two (or more) contacts are located within the target VTA, but neither is in a position to adequately stimulate the target VTA without spreading stimulation into neighboring side effect regions. A possible solution is to balance stimulation through the two contacts, possibly with unequal stimulus amplitudes, such that the target VTA is maximally stimulated.

The optimization method 214 can also employ a contact spacing search 232 to define a contact spacing that further maximizes the design VTA coverage with respect to the target VTA 206. Based on current steering analysis, there exists a contact spacing that maximizes VTA coverage along the trajectory of the electrode shaft. The optimization method 214 can employ the contact spacing search 232, such as in situations when more than one electrode contact will be activated to supply electric fields that may interact spatially and/or temporally. As one example, the optimization method 214 can activate the contact spacing search 232 to evaluate the effects of current-steering, such as in situations when the top scoring electrode design fails to meet a minimum score relative to the target VTA 206.

As one example, the contact spacing search 232 can search the parameterization space 202 according to spatially and/or temporally overlapping electric fields generated from multiple electrodes. The contact spacing search 232 can score the resulting design VTAs to determine which design or set of electrode designs having multiple contacts with independently controllable sources, best matches the target VTA. It should be noted that the electrode structure search 218 can be implemented as part of or in conjunction with the contact spacing search 232. As a result, the combination of electrode structure search 218 and the contact spacing search 232 can be employed to identify a contact spacing in conjunction with other electrode structure parameters (e.g., height and diameter for each contact) 208 that will afford a maximal VTA coverage along the trajectory of the electrode shaft. Thus, the contact spacing search 232 can be utilized to adjust the spacing between one or more pairs of electrodes in the electrode design 204 to determine spacing parameters for the electrode design that provides a design VTA 216 that more closely matches the target VTA 206.

The optimization method 214 can evaluate the impact of electrode trajectory variability and electrode location variability with respect to the added VTA coverage that can be attained with current steering contacts. The contact spacing search 232 can result in the electric field model 220 representing two or more electric field distributions, which can overlap according to the spacing and charge distribution of the respective fields. The spacing between electrode contacts can be defined in the parameterization space 202 by appropriate spacing parameters defined in the electrode structure parameters 208. Those skilled in the art will understand ways to construct appropriate electric field model 220 for the multiple contact electrode based on the teachings contained herein.

The variability adjustment 230 can also be utilized in conjunction with the contact spacing search 232 and the resulting multi-contact electrode design 204, similar to as described with respect to the single contact methodology. The variability adjustment component can thus identify a theoretically optimal trajectory that should be used with the determined optimal contact design and contact spacing (e.g., as defined by the electrode structure parameters 208 of the resulting electrode design 204).

In view of the foregoing, it will be appreciated that the design system 200 thus can provide a nuclei-specific single contact electrode design or a multiple contact design that is customized to the anatomical and electrical constraints of the target nucleus (e.g., the STN or Gpi or other neural tissue site, such as the spinal cord or a peripheral nerve). By also accounting for the potential variability in electrode placement and trajectory, such an electrode design should afford increase resilience to surgical placement variability while also maximizing VTA coverage for the target VTA.

As described herein, the resulting stimulation parameters for the electrode design can be employed to program an IPG or other stimulation device for applying stimulation to an electrode constructed according to the structural parameters, thereby achieving neurostimulation that substantially matches the target VTA.

Those skilled in the art will further appreciate that the design system 200 thus can provide a VTA-specific single contact electrode design or a multiple contact design that is customized to the anatomical and electrical constraints of the target nucleus (e.g., the STN or Gpi or other neural tissue site such as the spinal cord or a peripheral nerve). Additional information about how to design an electrode for a patient-specific target VTA is disclosed in the above-incorporated U.S. patent application Ser. No. 11/606,260. By also accounting for the potential variability in electrode placement and trajectory, such an electrode design should afford increase resilience to surgical placement variability while also maximizing VTA coverage of the target VTA. As described herein, the resulting stimulation parameters for the electrode design 204 can be employed to program an IPG or other stimulation device for applying stimulation to an electrode constructed according to the structural parameters, thereby achieving neurostimulation that substantially matches the target VTA 206.

By way of example, the electrode design 204, including stimulation parameters, can be communicated via an interface 236 to an IPG 238. For instance, the interface 236 can be implemented as a physical communication interface (e.g., including an electrically conductive or optical link) or a wireless communication interface (e.g., Bluetooth, or an inductive coupling). The IPG 238 can be programmed via the interface 236 prior to implanting the IPG or post-implantation. Those skilled in the art will understand and appreciate various types of connections and communication protocols that can be utilized for programming the IPG 238 with stimulation parameters, which may involve commercially available and proprietary methods. Additionally, the system 200 can have more than one interface capable of programming the IPG, a selected one of such interfaces can vary depending on the type of IPG and whether it has been implanted in vivo.

In view of the foregoing, it will be appreciated that additional variations in the VTA shape can be achieved by adjusting other design parameters, such as the number of contacts and spacing, the electrical stimulation parameters and the like. Those skilled in the art will appreciate that the methods and systems described herein can be employed to customize an electrode design 204 to maximize VTA spread for a given target nucleus. While the foregoing approach has been described with respect to electrical stimulation, those skilled in the art will understand that the approach is equally applicable to localized chemical stimulation of tissue in the nervous system.

Figure 14:
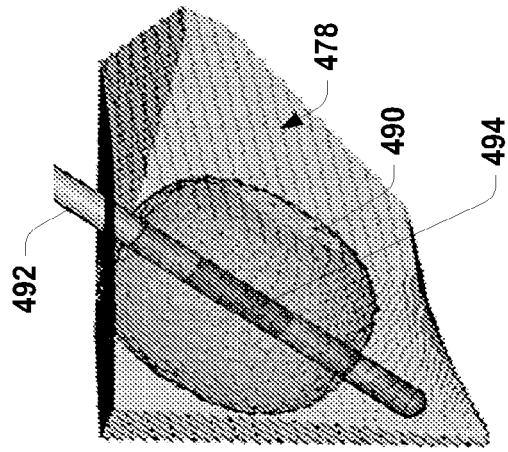
FIG. 14 depicts an image representing an example design VTA superimposed on the target VTA of FIG. 12 for a second electrode design.
Figure 13:
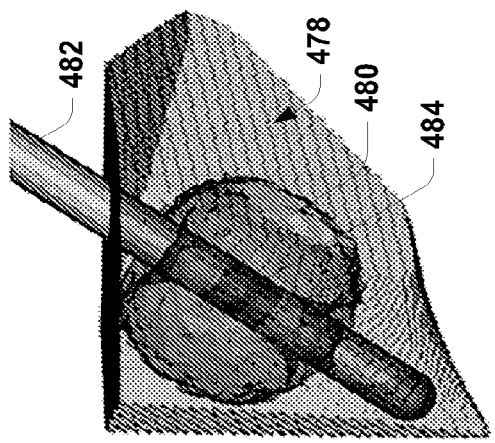
FIG. 13 depicts an image representing an example design VTA superimposed on the target VTA of FIG. 12 for a first electrode design.
Figure 12:
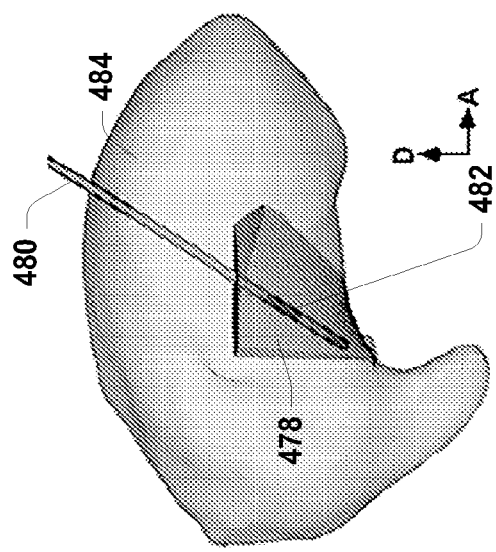
FIG. 12 depicts an image representing an example target VTA in the thalamus.

By way of further example, FIGS. 12, 13 and 14 demonstrate the effects of electrode geometry on VTA for a particular nucleus, namely the ventral intermediate nucleus of the thalamus (VIM) 478. For instance, FIG. 12 depicts an electrode 480 having a single contact 482 inserted into the thalamus 484. In the example of FIG. 12 the electrode is positioned at the anatomical center of the VIM 478. The VIM is a long narrow nucleus measuring approximately 8 mm (dorsal-ventral) by approximately 3 mm (anterior-posterior) by approximately 12 mm (medial-lateral).

FIG. 13 depicts a VTA 480 for an electrode 482 having first electrode design parameters. In the example of FIG. 13, the electrode 482 includes a contact 484 that corresponds to a standard electrode contact geometry (e.g., having a height of approximately 1.5 mm, diameter of approximately 1.27 mm, providing a surface area≈6 mm$^2$), with stimulation settings of −1 V and 90 μs pulse width at 130 Hz. The aspect ratio (d/h) of the electrode contact 484 is approximately 0.4. The electrode design of FIG. 19 produces the VTA 480 to fills approximately 26% of the VIM 478 before spreading outside the target VTA defined by the VIM.

Figure 20:
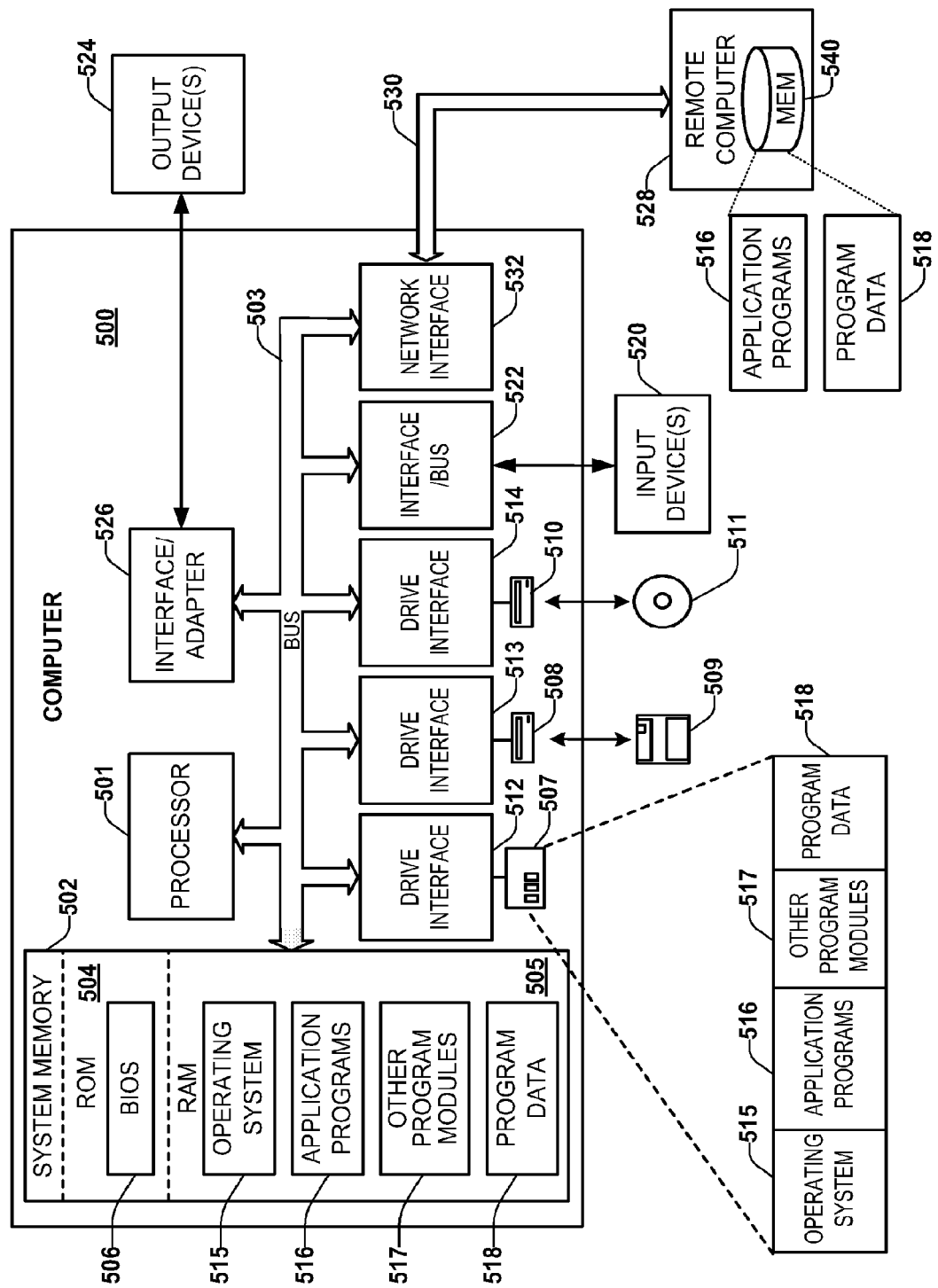
FIG. 20 depicts an example computer environment that can be used to perform methods and processes according to an aspect of the invention.

FIG. 14 depicts a VTA 490 for an electrode 492 having a second (customized) electrode design parameters, which are different from those of the electrode 482 of FIG. 13, such as may be determined according to an aspect of the invention. In the example of FIG. 20, the electrode includes a contact 494 that is also positioned at the anatomical center of the VIM. The electrode contact 494 is designed with a diameter of approximately 0.75 mm and a height of approximately 2.54 mm height to provide an aspect ratio of approximately 0.4, which more closely matches the aspect ratio of the VIM 478 than the example electrode in the example of FIG. 13. For sake of comparison, the electrode contact 494 has approximately the same contact surface area as the example of FIG. 13 and depicts a corresponding design VTA 490 under the same stimulation (stimulation voltage of about −1 V and 90 μs pulse width). The design of FIG. 14 conditions results in better stimulation of the VIM 478 by producing a VTA that fills 33% of the volume, which is about a 28% increase compared to the VTA 480 in the example of FIG. 13. Additionally, the custom electrode design 492 can result in approximately 7% more stimulation of the VIM 478 with no increase in spread outside the boundary of the target VTA defined by the VIM.

FIG. 15 depicts example data from stimulation testing at one electrode contact in one patient (in total 163 stimulation parameter settings were tested across 6 patients), such as can be employed to provide patient data for use in constructing the VTA data structure based on similar data acquired for a plurality of patients. The DBS data were acquired with a fixed stimulation frequency of 130 Hz and a fixed stimulus pulse width of 0.06 ms.

FIG. 15A depicts quantitative data for rigidity measurements that were acquired with a clinical impedance measurement device (model RA-1, NeuroKinetics). In FIG. 15A, higher values of mechanical impedance represent greater rigidity.

FIG. 15B depicts example data for finger tapping bradykinesia measurements that were acquired with solid state gyroscopes (model G-1, NeuroKinetics). In FIG. 15B, higher values represent lower bradykinesia.

FIG. 15C represents Paresthesia data rated on a 10 point scale, as reported by the patient. FIGS. 15D and 15E represent rigidity Bradykinesia data, respectively, that have been rescored on a normalized scale from 1 to −1. Scores above 0 indicate improvement and scores below 0 indicate worsening relative to the OFF DBS baseline. Shaded areas indicate stimuli above the paresthesia threshold.

FIG. 16 (including FIGS. 16A-K) depicts examples of patient-specific stimulation models that can be employed in connection with determining a target VTA according to an embodiment of the invention. FIG. 16A illustrates 3D nuclei (e.g. thalamus and STN) that were fit to the pre-operative MRI of each subject. FIG. 16B illustrates a pre-operative MRI that has been co-registered with a post-operative MRI to identify the implanted DBS electrode location. FIG. 16C illustrates, for each tested hemisphere (n=7), the electrode location defined relative to the pertinent nuclei.

FIG. 16D illustrates each patient-specific model transformed into the context of a single atlas brain. The atlas brain included both anatomical and diffusion tensor imaging data and was used to predict neural activation from the stimulation protocol.

FIG. 16E illustrates DTI-based conductivity tensors with color indicating fractional anisotropy describing the tissue electrical properties. FIG. 16F depicts each patient-specific model having a unique DBS electrode location. FIG. 16G illustrates that each experimentally tested stimulation parameter setting results in a unique voltage distribution, which varies according to the stimulation parameters. FIG. 16H illustrates that a theoretical volume of tissue activated (VTA) by each tested setting (n=163) was calculated.

Each VTA was assigned a clinical score, as shown in FIG. 16I for rigidity, in FIG. 16J for bradykinesia, and in FIG. 16K for paresthesia. Those skilled in the art will understand and appreciate that each VTA can also (or alternatively) be provided other clinically relevant scores, including quantitative and/or qualitative assessments of the patient's condition.

FIG. 17 (including FIGS. 17A through 17D) depicts examples of clinical outcomes for different electrode placements and stimulation parameters. FIG. 17A illustrates DBS electrode locations for all patients (n=7 hemispheres) in the context of the atlas brain. FIG. 17B depicts VTAs generated for all electrode locations and stimulation protocols (n=163 VTAs), shown superimposed on each other. Each VTA had an assigned clinical score for rigidity, bradykinesia, and paresthesia.

Figure 17A:
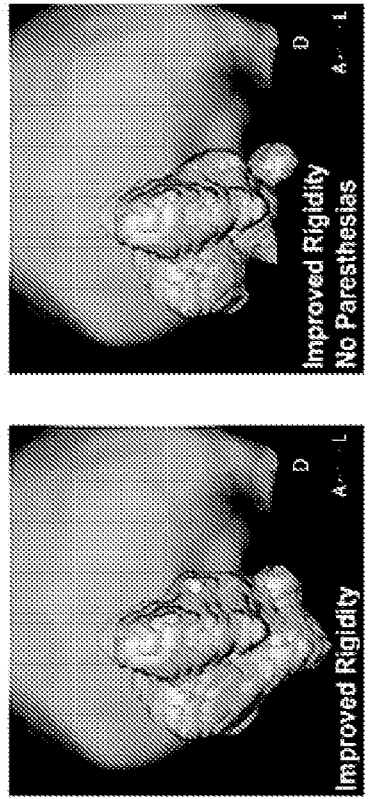
FIGS. 17A through 17D depict examples of clinical outcomes for a given patent for a plurality of VTAs, such as can be utilized for constructing a VTA data structure according to an aspect of the invention.
Figure 17C:
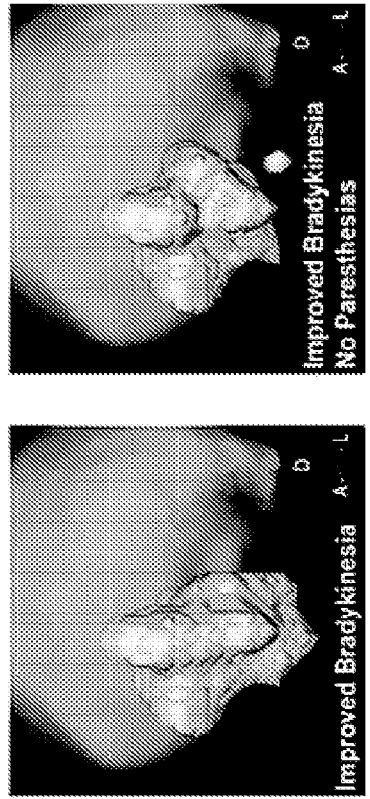
Figure 17B:
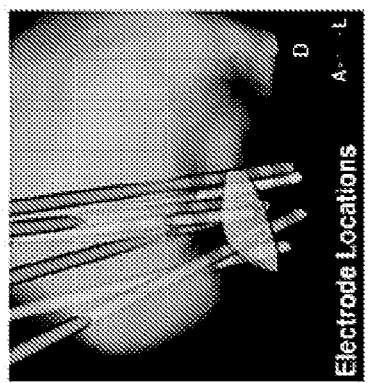
Figure 17D:
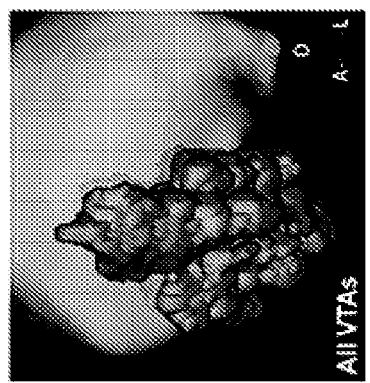

FIG. 17C depicts summated activation volume associated with improved rigidity. FIG. 17D depicts summated activation volume associated with improved bradykinesia. The left column of FIGS. 17C and 17D shows all VTAs with improvement in rigidity or bradykinesia, while the right column of FIGS. 17C and 17D shows only VTAs corresponding to stimulation settings that did not also generate paresthesias.

FIG. 18 (including FIGS. 18A through 18F) depicts probabilistic stimulation target VTAs. Each target VTA can be assigned a clinical score for rigidity and bradykinesia as well as for other conditions. Each VTA was voxelized onto a 3D grid of 0.5 mm cubes that encompassed the entire brain region evaluated with DBS. A statistically defined level of clinical improvement was then defined for each voxel based on the VTAs that overlapped with that voxel. In FIGS. 18A through 18F, the blue volumes indicate the stimulation region associated with at least 50% (FIG. 18A) or 75% (FIG. 18B) improvement in normalized clinical scores of rigidity. The pink volumes indicate 50% (FIG. 18C) or 75% (FIG. 18D) improvement in bradykinesia. FIGS. 18E and 18F illustrate combined rigidity and bradykinesia volumes by aggregating the respective volumes determined for FIGS. 18A and 18C as well as the volumes from FIGS. 18B and 18D.

FIG. 19 is a table demonstrating examples of the type of information that can be used to populate the VTA data structure. While the table of FIG. 19 depicts patient data for 6 patients and 163 VTAs, it will be appreciated that the VTA data structure can (and typically) be generated based on a larger population size. However, six or fewer may suffice to provide a statistical database.

In FIG. 19, for each patient, an indication of primary symptoms is included. Also included are the patient's age, sex, years post-surgical, the hemisphere stimulated. Electrode and stimulation parameters are also provided, including the impedance and voltage range for each of a plurality of contacts for each of the VTAs. In the example table of FIG. 19, the electrodes include four contacts although greater or fewer contacts can be employed. Additionally, each patient could be treated with a different electrode configuration.

As depicted, data is acquired for a number of VTAs for each patient, such as according to the electrode placement and stimulation parameters described herein. One or more clinical scores (not shown) are also associated with each of the VTAs for each patient in the VTA data structure. For example, each VTA can be assigned a clinical score, such as for rigidity, for bradykinesia, and for paresthesia (e.g., see FIGS. 16I, 16J and 16K). Those skilled in the art will appreciate various clinical rating systems (including qualitative and/or quantitative metrics) that can be employed to score these as well as other patient conditions for each VTA.

FIG. 27 is a table demonstrating examples of the type of information that can be used to populate the VTA data structure for spinal cord stimulation. While the table of FIG. 19 depicts patient data for 6 patients and 163 VTAs, it will be appreciated that the VTA data structure can (and typically will) be generated based on a larger population size. However, six or fewer may suffice to provide a statistical database.

For each patient, the location of the pain is indicated. Also included are the patient's age, sex, and number of years post-surgical. Electrode stimulation parameters are also provided, including the impedance and voltage ranges for each of the contacts. In the example table of FIG. 27, the electrodes include four contacts each, although greater or fewer contacts can be used. Additionally, each patient could be treated with a different electrode configuration.

As depicted in FIG. 27, data is acquired for a number of VTAs for each patient, such as according to the electrode placement and stimulation parameters described herein. One or more clinical scores (not shown) are also associated with each of the VTAs for each patient in the VTA data structure. For example, each VTA can be assigned a clinical score, such as for the amount of pain or parasthesia that the pain experiences. Those skilled in the art will appreciate various clinical rating systems (including qualitative and/or quantitative metrics) that can be employed to score these as well as other patient conditions for each VTA.

In view of the foregoing, FIG. 20 illustrates one example of a computer system 500 that can be employed to execute one or more embodiments of the invention by storing and/or executing computer executable instructions. Computer system 500 can be implemented on one or more general purpose networked computer systems, embedded computer systems, routers, switches, server devices, client devices, various intermediate devices/nodes or stand alone computer systems. Additionally, computer system 500 can be implemented on various mobile clients such as, for example, a personal digital assistant (PDA), laptop computer, pager, and the like, provided it includes sufficient processing capabilities.

Computer system 500 includes processing unit 501, system memory 502, and system bus 503 that couples various system components, including the system memory, to processing unit 501. Dual microprocessors and other multi-processor architectures also can be used as processing unit 501. System bus 503 may be any of several types of bus structure including a memory bus or memory controller, a peripheral bus, and a local bus using any of a variety of bus architectures. System memory 502 includes read only memory (ROM) 504 and random access memory (RAM) 505. A basic input/output system (BIOS) 506 can reside in ROM 504 containing the basic routines that help to transfer information among elements within computer system 500.

Computer system 500 can include a hard disk drive 507, magnetic disk drive 508, e.g., to read from or write to removable disk 509, and an optical disk drive 510, e.g., for reading CD-ROM disk 511 or to read from or write to other optical media. Hard disk drive 507, magnetic disk drive 508, and optical disk drive 510 are connected to system bus 503 by a hard disk drive interface 512, a magnetic disk drive interface 513, and an optical drive interface 514, respectively. The drives and their associated computer-readable media provide nonvolatile storage of data, data structures, and computer-executable instructions for computer system 500. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the present invention.

A number of program modules may be stored in drives and RAM 505, including operating system 515, one or more application programs 516, other program modules 517, and program data 518. The application programs and program data can include functions and methods programmed to determine a target VTA as well as to determine design parameters for stimulation of the target VTA in a given patient, such as shown and described herein.

A user may enter commands and information into computer system 500 through one or more input devices 520, such as a pointing device (e.g., a mouse, touch screen), keyboard, microphone, joystick, game pad, scanner, and the like. For instance, the user can employ input device 520 to edit or modify a domain model. Additionally or alternatively, a user can access a user interface via the input device to create one or more instances of a given domain model and associated data management tools, as described herein. These and other input devices 520 are often connected to processing unit 501 through a corresponding port interface 522 that is coupled to the system bus, but may be connected by other interfaces, such as a parallel port, serial port, or universal serial bus (USB). One or more output devices 524 (e.g., display, a monitor, printer, projector, or other type of displaying device) is also connected to system bus 503 via interface 526, such as a video adapter.

Computer system 500 may operate in a networked environment using logical connections to one or more remote computers, such as remote computer 528. Remote computer 528 may be a workstation, computer system, router, peer device, or other common network node, and typically includes many or all the elements described relative to computer system 500. The logical connections, schematically indicated at 530, can include a local area network (LAN) and a wide area network (WAN).

When used in a LAN networking environment, computer system 500 can be connected to the local network through a network interface or adapter 532. When used in a WAN networking environment, computer system 500 can include a modem, or can be connected to a communications server on the LAN. The modem, which may be internal or external, can be connected to system bus 503 via an appropriate port interface. In a networked environment, application programs 516 or program data 518 depicted relative to computer system 500, or portions thereof, may be stored in a remote memory storage device 540.

What have been described above are examples and embodiments of the invention. It is, of course, not possible to describe every conceivable combination of components or methodologies for purposes of describing the invention, but one of ordinary skill in the art will recognize that many further combinations and permutations of the present invention are possible. Accordingly, the invention is intended to embrace all such alterations, modifications and variations that fall within the scope of the appended claims. In the claims, unless otherwise indicated, the article "a" is to refer to "one or more than one."

What is claimed is:

1. A computer-implemented method comprising:
storing in a memory device a volume of tissue activation (VTA) data structure that is derived from analysis of a plurality of patients;
receiving, by a computer processor, patient data for a given patient, the patient data representing an assessment of a patient condition; and
evaluating, by the computer processor, the VTA data structure relative to the patient data to determine a target VTA for achieving a desired therapeutic effect for the given patient.

2. The method of claim 1, wherein the target VTA has a boundary defined in a three-dimensional coordinate system for the patient.

3. The method of claim 1, further comprising determining at least one of a structural parameter and a stimulation parameter that can provide a design VTA that substantially matches the target VTA.

4. The method of claim 3, wherein the structural parameter comprises electrode design parameter data and the stimulation parameter comprises electrical stimulation parameter data.

5. The method of claim 4, further comprising selecting an electrode design according to the electrode design parameter data.

6. The method of claim 5, further comprising programming an implantable pulse generator according to the electrical stimulation parameter data for the selected electrode design such that application of the respective electrical stimulation data to an implanted electrode structure results in stimulation of tissue that substantially achieves the target VTA for the given patient.

7. The method of claim 3, further comprising searching through a plurality of VTAs by adjusting the at least one of a structural parameter and a stimulation parameter to determine the design VTA that best matches the target VTA for achieving the desired therapeutic effect.

8. The method of claim 7, further comprising scoring each of the plurality of VTAs as a prospective design VTA to provide a score that characterizes an amount of overlap between each prospective design VTA and the target VTA.

9. The method of claim 8, wherein the target VTA has a boundary defined in a three-dimensional coordinate system for the patient the scoring, the method further comprising applying a penalty to the scoring according to a spread of the design volume of tissue activation that extends outside the boundary of the target VTA.

10. The method of claim 9, wherein the score is determined according to:

$$\text{Score} = (\text{VTA}_{in\ target}/\text{VTA}_{target}) * (1 - \text{VTA}_{out\ target}/X\text{volume}),$$

where:
$\text{VTA}_{in\ target}$ corresponds to the portion of the design VTA that resides within the target VTA,
$\text{VTA}_{out\ target}$ corresponds to the portion of the design VTA that resides outside of the target VTA, and
Xvolume defines the penalty for stimulation spread outside of the target VTA.

11. The method of claim 3, further comprising morphing the design VTA to fit the corresponding anatomical region of the given patient and storing data representing the morphed design VTA to provide patient-specific data corresponding to the design VTA.

12. The method of claim 1, wherein the VTA data structure comprises a plurality of statistical atlases, each of the plurality of statistical atlases comprising data that statistically characterizes a therapeutic effect for a plurality of VTAs acquired for the plurality of patients.

13. The method of claim 12, wherein the data in the VTA data structure further comprises stimulation parameters associated with each of the plurality of VTAs.

14. The method of claim 12, wherein the data in the VTA data structure further comprises at least one clinical score associated with each of the plurality of VTAs.

15. The method of claim 12, wherein each of the statistical atlases further comprises a statistical representation of data that identifies a likelihood of desirable therapeutic effects associated with providing stimulation for each of the plurality of VTAs.

16. The method of claim 15, wherein each of the statistical atlases further comprises statistical information corresponding to negative or undesirable therapeutic effects associated with providing stimulation for each of the respective VTAs.

17. The method of claim 12, wherein the plurality of statistical atlases are hierarchically organized according to one or more categories and a plurality of subcategories.

18. The method of claim 17, wherein the one or more categories and the plurality of subcategories are based on at least one of symptoms and diseases.

19. The method of claim 12, wherein the plurality of statistical atlases are atlases of spinal cords.

20. The method of claim 1, further comprising updating the VTA data structure in response to acquiring clinical data for at least one additional patient.

21. The method of claim 1, wherein the tissue is the spinal cord.

22. A system for determining a volume of tissue activation for achieving a desired therapeutic effect for a given patient, the system comprising:
a volume of tissue activation (VTA) data structure stored in memory, the VTA data structure being derived from analysis anatomical and electrical data acquired for a plurality of patients;
patient data stored in the memory, the patient data representing an assessment of a patient condition for the given patient; and
a processor programmed to execute instructions for:
evaluating the VTA data structure relative to the patient data to determine a target VTA for achieving a desired therapeutic effect for the given patient, and
determining at least one of a structural parameter and a stimulation parameter that can provide a design VTA for the given patient that substantially matches the target VTA.

23. The system of claim 22, further comprising an interface configured for communicatively coupling the system to a stimulation device, the processor being programmed to program the stimulation device according to the stimulation parameter to achieve a desired therapeutic effect for the given patient.

24. The system of claim 22, wherein the processor is programmed to employ an optimization algorithm programmed to search through a plurality of VTAs in the VTA data structure by adjusting the at least one of a structural parameter and a stimulation parameter to determine the design VTA that best matches the target VTA for achieving the desired therapeutic effect.

25. The system of claim 22, wherein the tissue is the spinal cord.

26. A computer-implemented method comprising:
storing in memory a volume of tissue activation (VTA) data structure that is derived from analysis of a plurality of patients, wherein the VTA data structure includes a statistical atlas mapping, for sub-regions of the atlas, respective probabilities for stimulation at the respective sub-regions to achieve a therapeutic effect;
receiving, by a computer processor, patient data for a given patient, the patient data representing an assessment of a patient disease condition; and
constructing, by the computer processor, a target VTA based on the probabilities mapped in the atlas and the received patient data.

27. The method of claim 26, wherein the atlas is generated based on analysis of therapeutic effect of a plurality of VTAs of a patient population.

28. The method of claim 27, wherein each voxel of the atlas is assigned a respective therapeutic probability value based on information pertaining to those of the plurality of VTAs of which the respective voxel is a part.

29. The method of claim 26, wherein:
- the VTA data structure includes a plurality of statistical atlases of which the statistical atlas is one;
- each of the atlases maps, for sub-regions of the atlas, respective probabilities for stimulation at the respective sub-regions to achieve a respective therapeutic effect to which the respective atlas pertains; and
- the plurality of atlases are hierarchically organized according to one or more categories and a plurality of subcategories.

* * * * *

UNITED STATES PATENT AND TRADEMARK OFFICE
CERTIFICATE OF CORRECTION

PATENT NO. : 8,812,126 B2
APPLICATION NO. : 13/765306
DATED : August 19, 2014
INVENTOR(S) : Christopher R. Butson et al.

It is certified that error appears in the above-identified patent and that said Letters Patent is hereby corrected as shown below:

In the Specification

Column 1, Lines 33-35, should read:
This invention was made with government support under NS059736 awarded by the National Institutes of Health. The government has certain rights in the invention.

Signed and Sealed this
Twenty-fourth Day of May, 2022

Katherine Kelly Vidal
*Director of the United States Patent and Trademark Office*